United States Patent
Murphy et al.

(10) Patent No.: US 12,280,177 B2
(45) Date of Patent: Apr. 22, 2025

(54) FUNCTIONALIZATION OF PLANT TISSUES FOR HUMAN CELL EXPANSION

(71) Applicants: Wisconsin Alumni Research Foundation, Madison, WI (US); ARKANSAS STATE UNIVERSITY—JONESBORO, State University, AR (US); Worcester Polytechnic Institute, Worcester, MA (US)

(72) Inventors: William L. Murphy, Waunakee, WI (US); Gianluca Fontana, Matera, WI (US); Joshua Gershlak, Melrose, MA (US); Glenn Gaudette, Holden, MA (US); Pam Weathers, Stow, MA (US); Tanja Dominko, Verona, MA (US); Marsha Rolle, Worcester, MA (US); Sarah Hernandez, Carver, MA (US); Carol Cramer, Jonesboro, AR (US); Luis Fabircio Medina-Bolivar, Memphis, TN (US); Bernard Binder, Pleasant Hill, CA (US)

(73) Assignees: Wisconsin Alumni Research Foundation, Madison, WI (US); ARKANSAS STATE UNIVERSITY—JONESBORO, State University, AR (US); Worcester Polytechnic Institute, Worcester, MA (US)

( * ) Notice: Subject to any disclaimer, the term of this patent is extended or adjusted under 35 U.S.C. 154(b) by 717 days.

(21) Appl. No.: 17/388,652

(22) Filed: Jul. 29, 2021

(65) Prior Publication Data
US 2022/0054708 A1    Feb. 24, 2022

Related U.S. Application Data

(63) Continuation of application No. 16/085,220, filed as application No. PCT/US2017/022336 on Mar. 14, 2017, now abandoned.

(60) Provisional application No. 62/462,653, filed on Feb. 23, 2017, provisional application No. 62/318,953, filed on Apr. 6, 2016, provisional application No. 62/307,771, filed on Mar. 14, 2016.

(51) Int. Cl.
| | |
|---|---|
| *A61L 27/36* | (2006.01) |
| *A61L 27/12* | (2006.01) |
| *A61L 27/22* | (2006.01) |
| *A61L 27/38* | (2006.01) |
| *A61L 27/54* | (2006.01) |
| *C12N 5/00* | (2006.01) |
| *C12N 5/04* | (2006.01) |

(52) U.S. Cl.
CPC ......... *A61L 27/3637* (2013.01); *A61L 27/12* (2013.01); *A61L 27/227* (2013.01); *A61L 27/3834* (2013.01); *A61L 27/54* (2013.01); *C12N 5/0068* (2013.01); *C12N 5/04* (2013.01); *A61L 2300/25* (2013.01); *A61L 2300/412* (2013.01); *A61L 2300/414* (2013.01); *C12N 2533/90* (2013.01); *C12N 2535/00* (2013.01)

(58) Field of Classification Search
CPC ......................... A61L 27/3637; C12N 5/0068
See application file for complete search history.

(56) References Cited

U.S. PATENT DOCUMENTS 12,123,026 B2 * 10/2024 Aisenbrey .......... G01N 33/5082

FOREIGN PATENT DOCUMENTS

WO      2016018145 A1    2/2016

OTHER PUBLICATIONS

Modulevsky et al., 2014, Apple Derived Cellulose Scaffolds for 3D Mammalian Cell Culture, PLOS One, 9(5): e97835 (10 pages).*
Place et al., 2009, Complexity in biomaterials for tissue engineering, Nature Materials, 8: 457-470.*
Mano et al., 2007, Natural origin biodegradable systems in tissue engineering and regenerative medicine: present status and some moving trends, J R Soc Interface, 4: 999-1030.*
Ding et al., Mussel-inspired polydopamine for bio-surface functionalization; Biosurf Biotribol, 2016, vol. 2, No. 4, pp. 121-136.
Fontana et al., Biofunctionalized Plants as Diverse Biomaterials for Human Cell Culture; Adv., Healthcare Mater: 2017, vol. 6, pp. 1601225—9-pages.
Gershlak et al., Crossing kingdoms: Using decellularized plants as perfusable tissue engineering scaffolds; Biomaterials, 2017, vol. 125, ppl 13-22.
Mano et al., Natural origin biodegradable systems in tissue engineering and regenerative medicine: present status and some moving trends; J. R. Soc. Interface, 2007, vol. 4, pp. 999-1030.
Modulevsky et al., Apple Derived Cellulose Scaffolds for 3D Mammalian Cell Culture, PLoS One, May 2014, vol. 9, No. 5, pp. e97835.

(Continued)

*Primary Examiner* — Amber D Steele
(74) *Attorney, Agent, or Firm* — Quarles & Brady, LLP

(57) ABSTRACT

Decellularized plant tissues and the use of these plant tissues as scaffolds are disclosed herein. Particularly, decellularized plant tissues are functionalized such to allow for human cell adhesion, thereby allowing for their use as scaffolds for human cells. These scaffolds can then be used in a number of applications/markets, including as research tools for tissue engineering, regenerative medicine, and basic cellular biology.

15 Claims, 36 Drawing Sheets

Specification includes a Sequence Listing.

(56) References Cited

OTHER PUBLICATIONS

Musilkova et al., Cell adhesion and growth enabled by biomimetic oligopeptide modification of a polydopamine-poly (ethylene oxide) protein repulsive surface; J. Mater Sci: Mater Med (2015), vol. 26, 253.

Place et al., Complexity in biomaterials for tissue engineering; Nature Materials; 2009, vol. 9, 14-pages.

Sigmaaldrich; Dulbecco's Modified Eagle's Medium (DME) Formulation; Feb. 22, 2016; 4-pages.

* cited by examiner

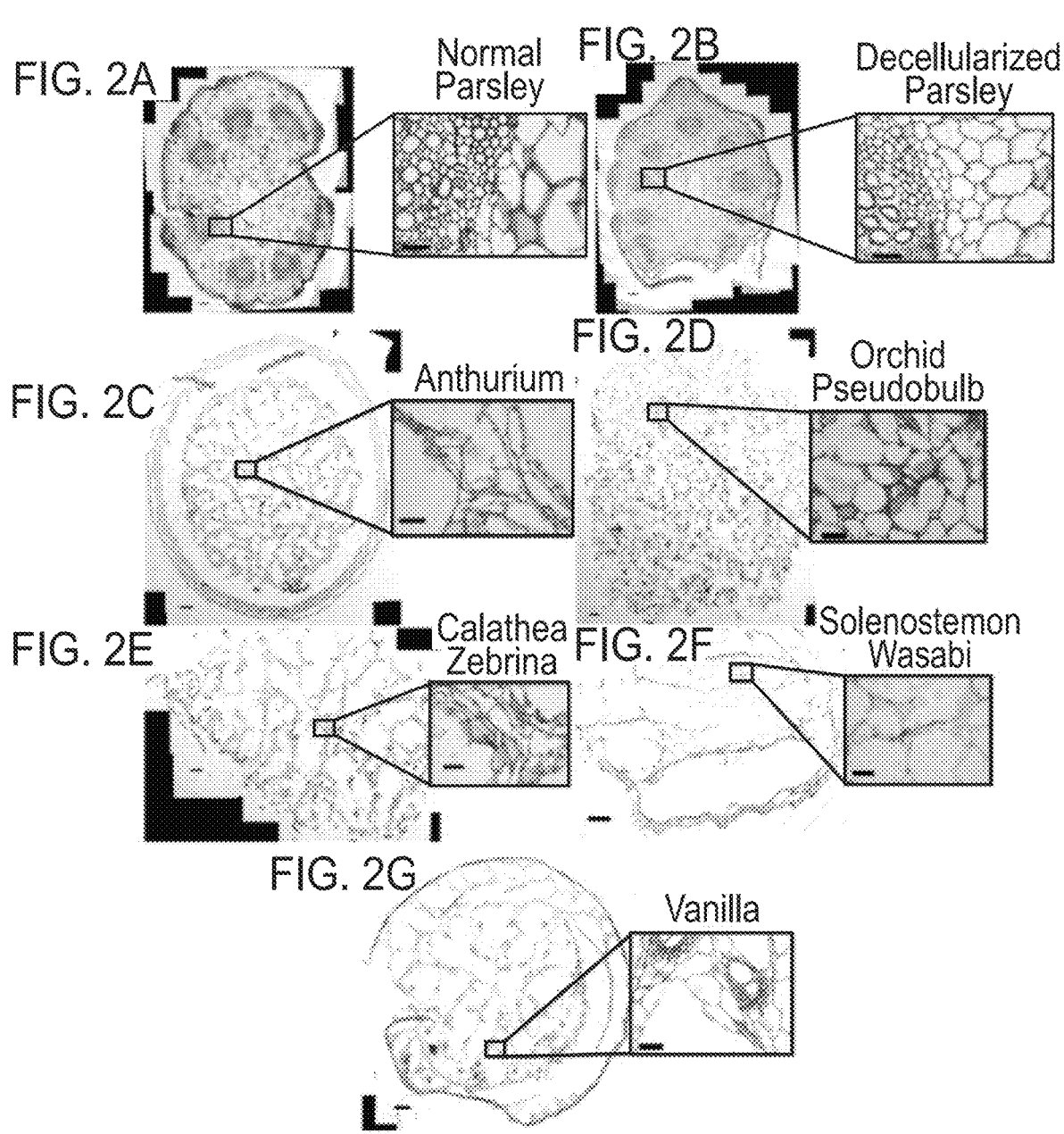

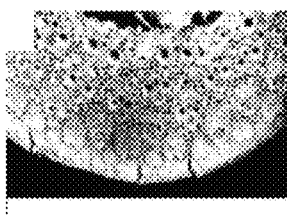 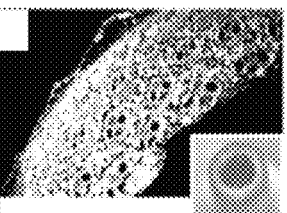 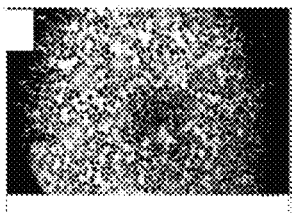 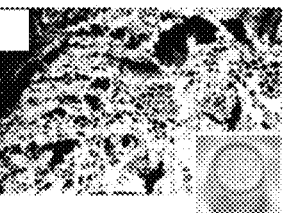
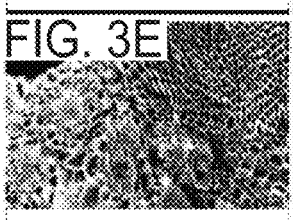 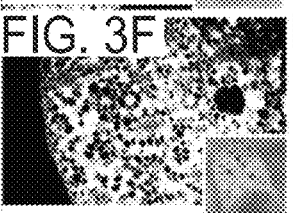 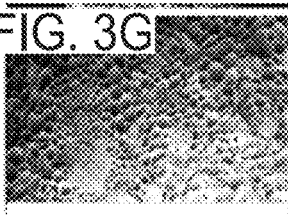 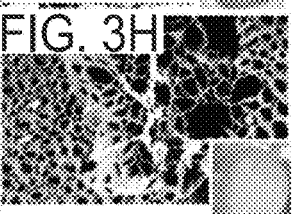
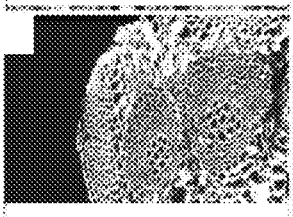 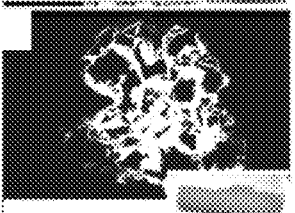 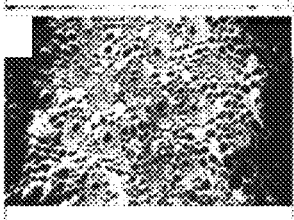 
FIG. 3A  FIG. 3B  FIG. 3C  FIG. 3D
FIG. 3E  FIG. 3F  FIG. 3G  FIG. 3H
FIG. 3I  FIG. 3J  FIG. 3K  FIG. 3L

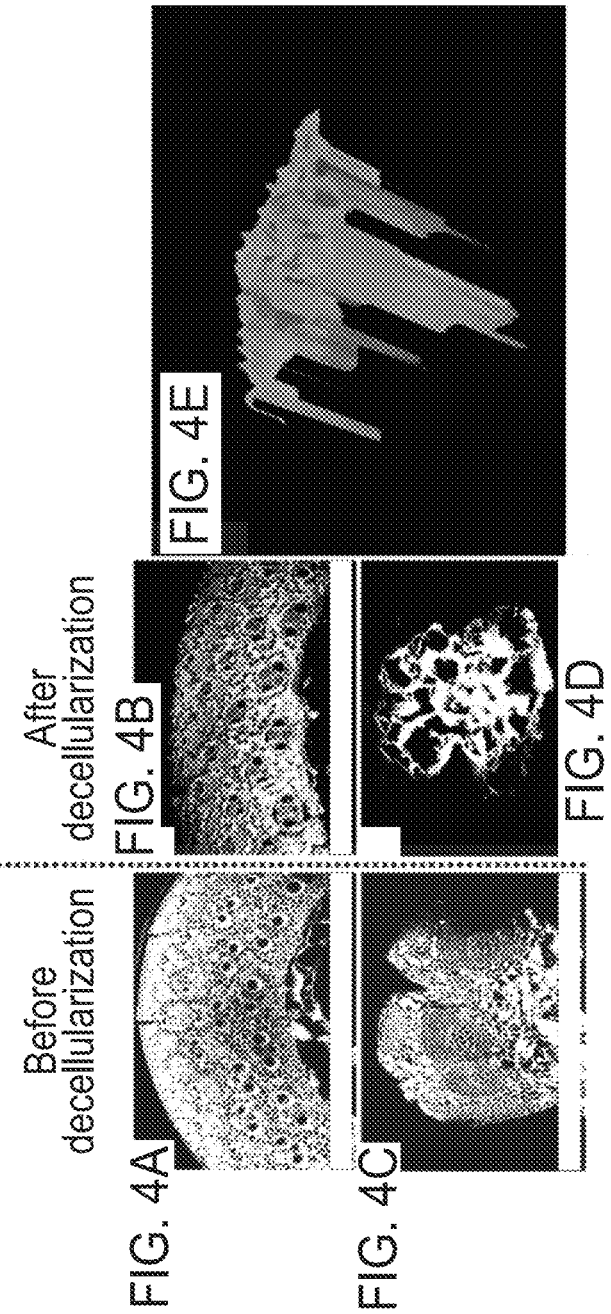

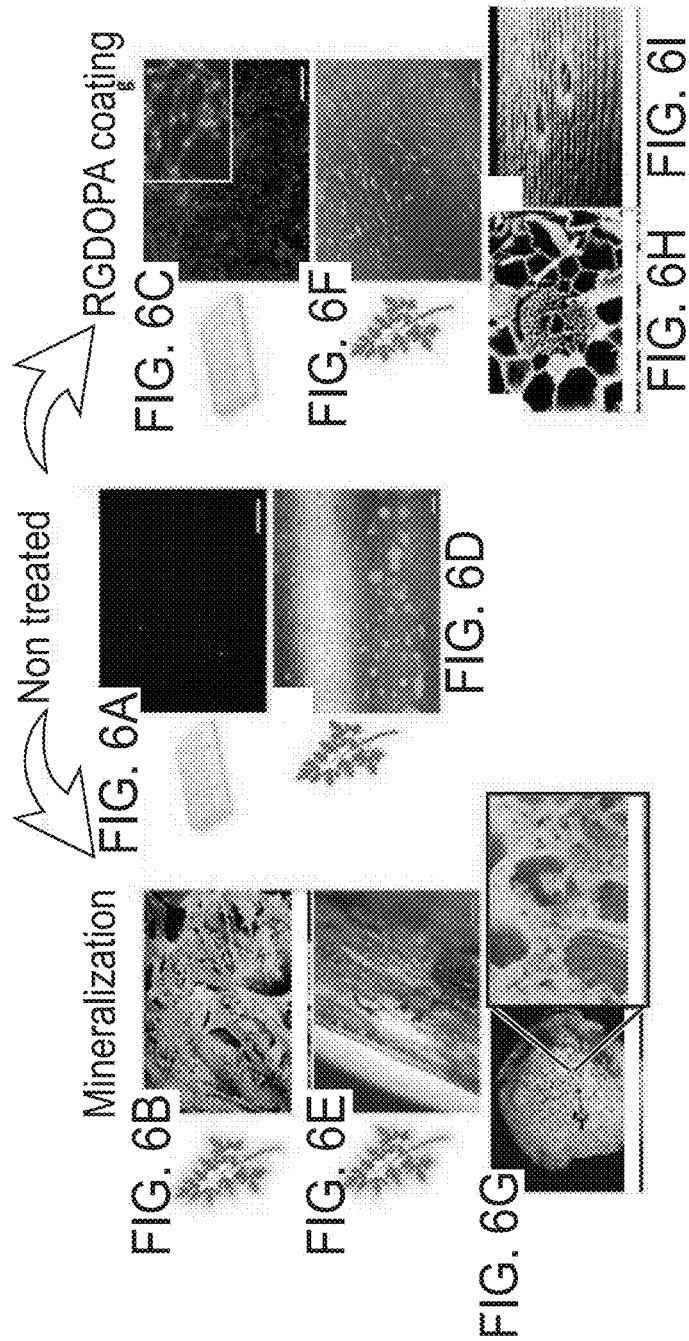

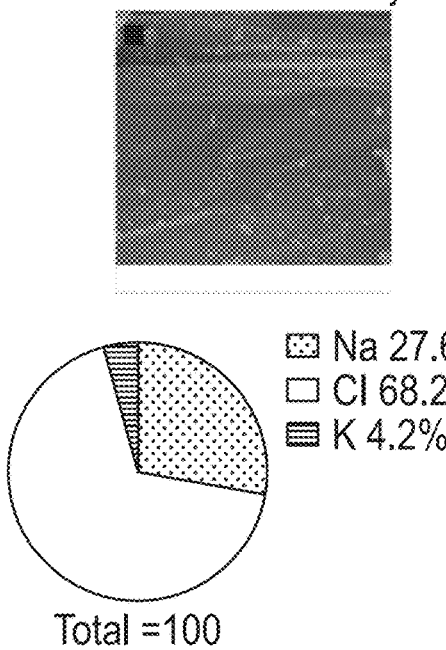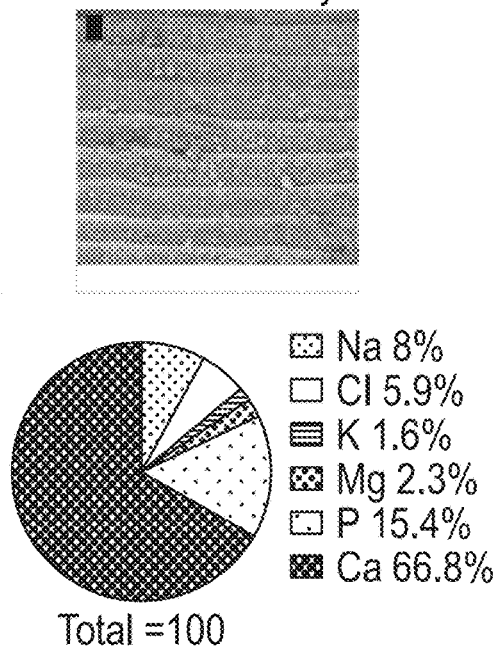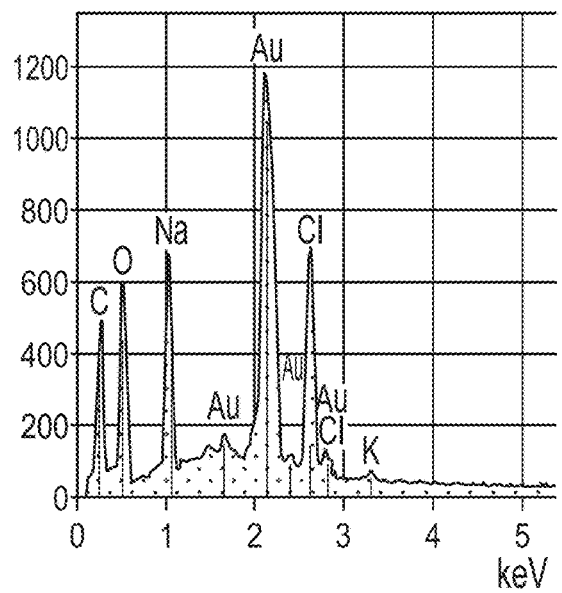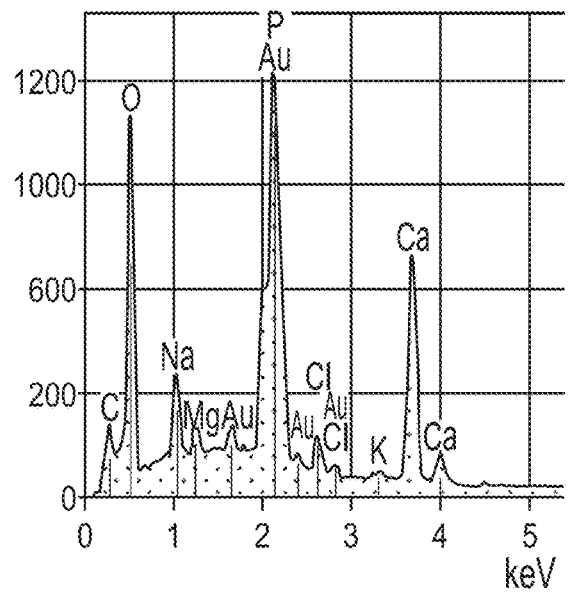
FIG. 8A      FIG. 8B

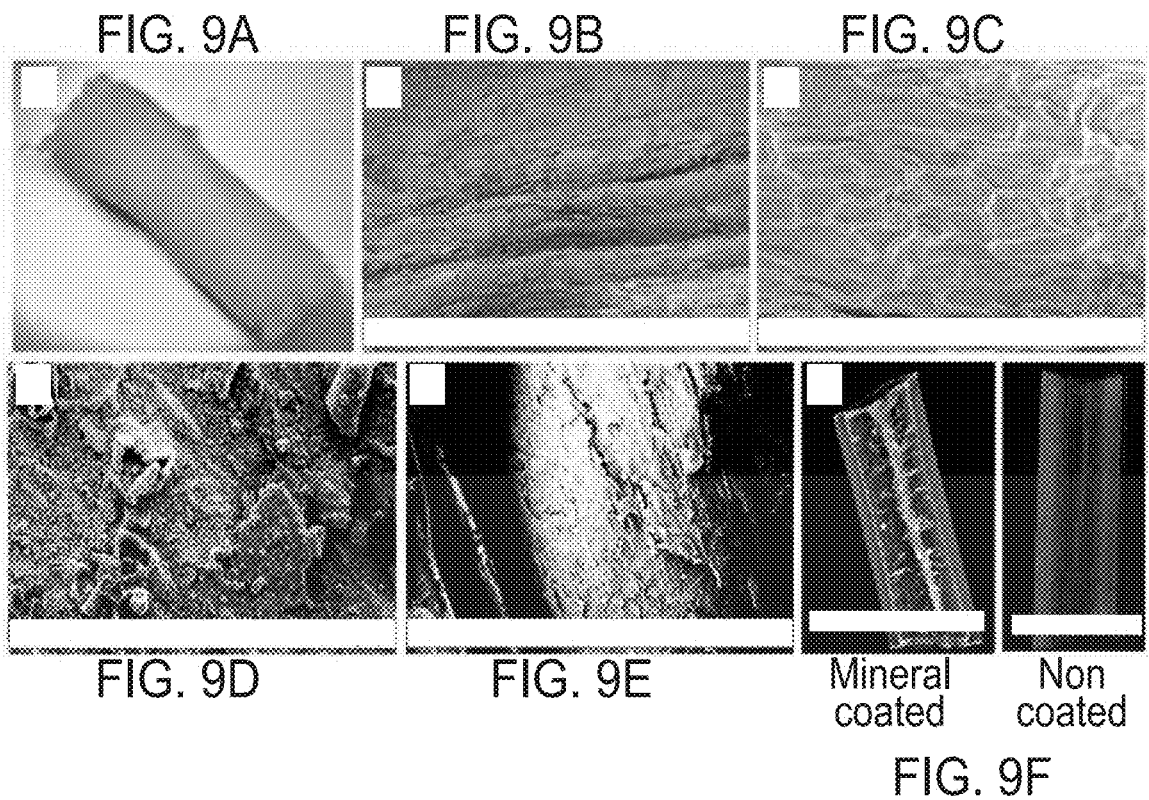

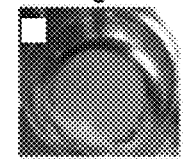 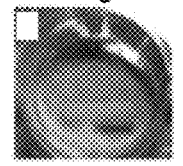 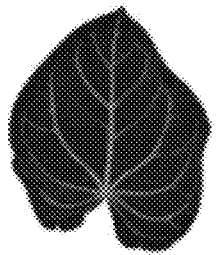 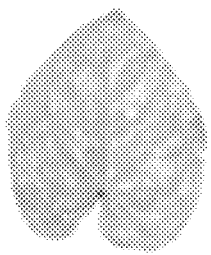
FIG. 11G  FIG. 11H  FIG. 11I
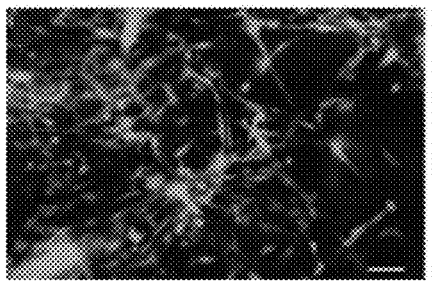 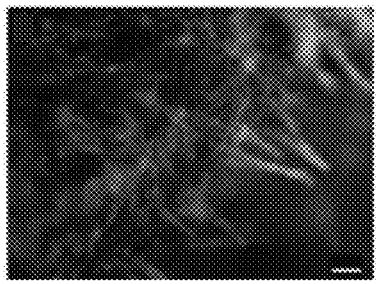 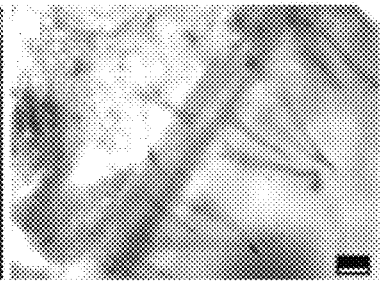
FIG. 11J  FIG. 11K  FIG. 11L

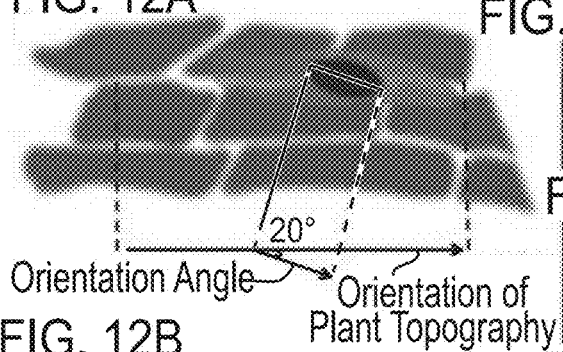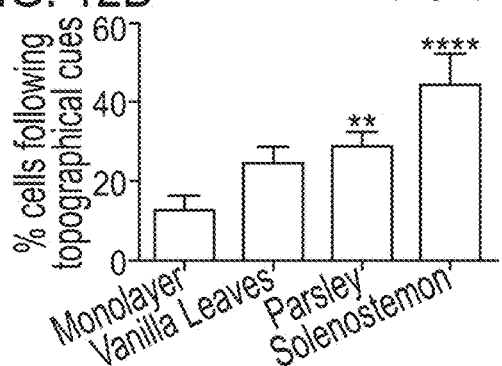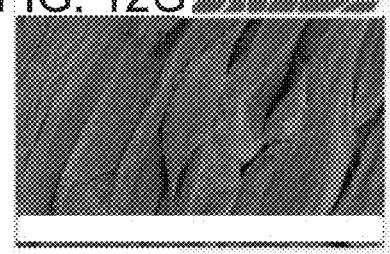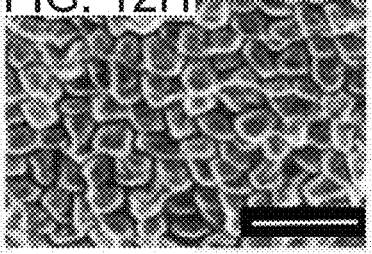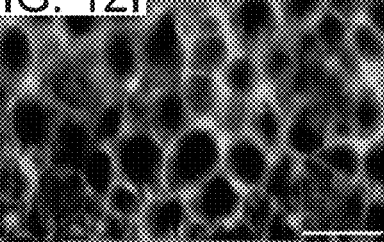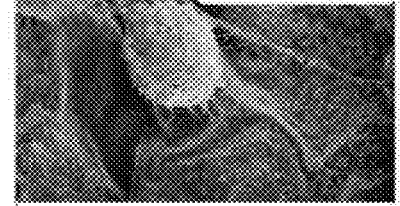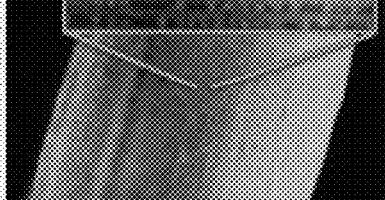

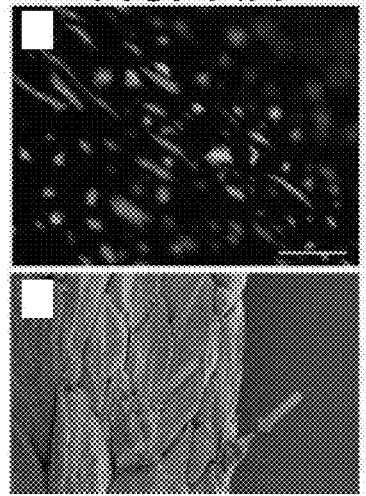 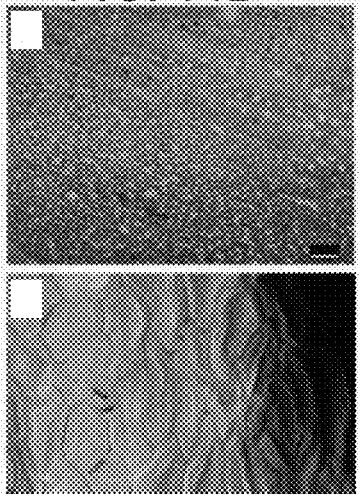 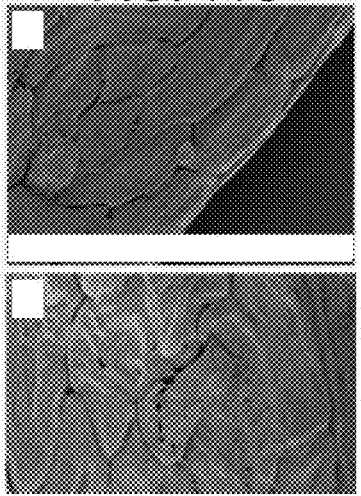
FIG. 14A  FIG. 14B  FIG. 14C
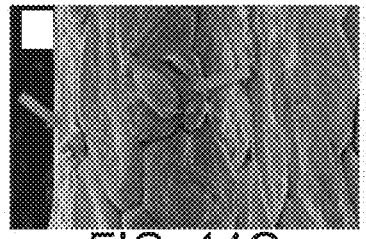 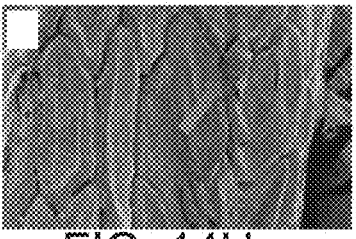 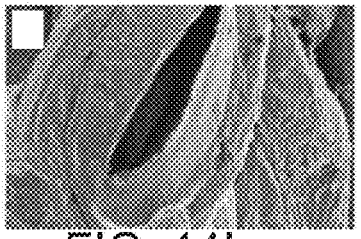
FIG. 14D  FIG. 14E  FIG. 14F
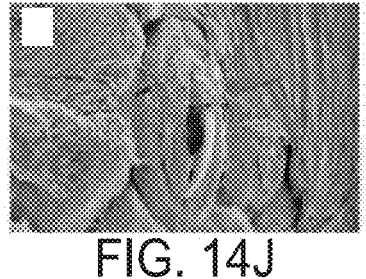 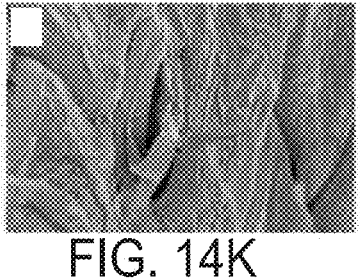 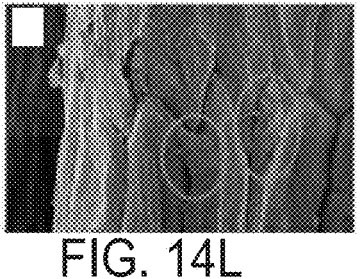
FIG. 14G  FIG. 14H  FIG. 14I
  
FIG. 14J  FIG. 14K  FIG. 14L Mammalian Plant

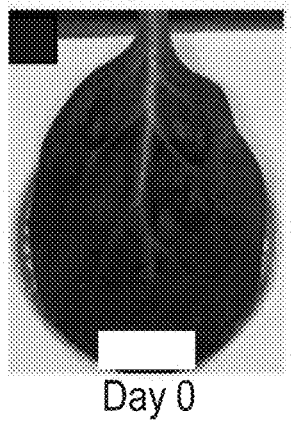 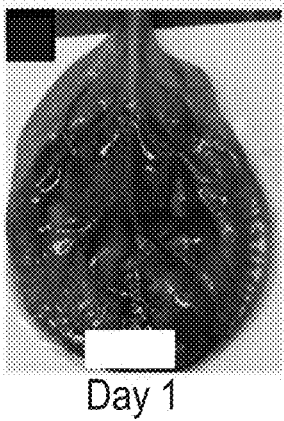 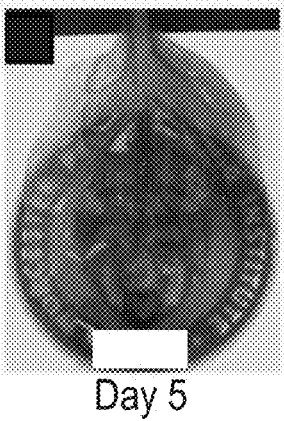 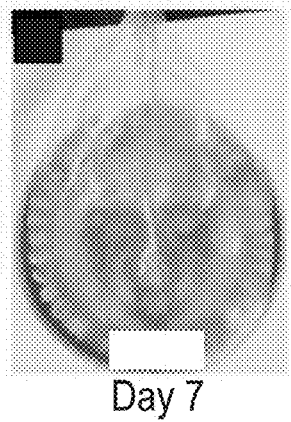
FIG.19A Day 0  FIG.19B Day 1  FIG.19C Day 5  FIG.19D Day 7

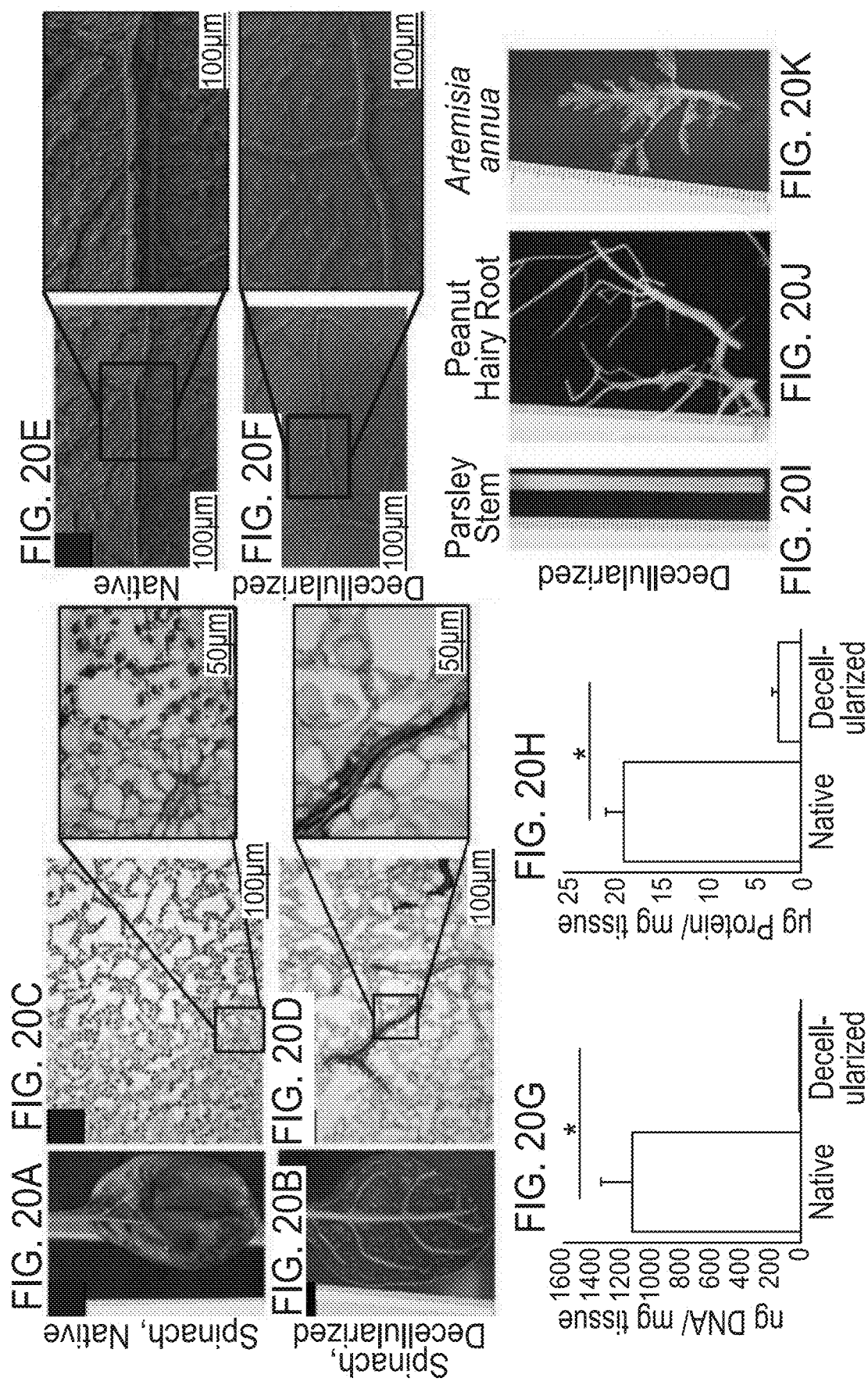

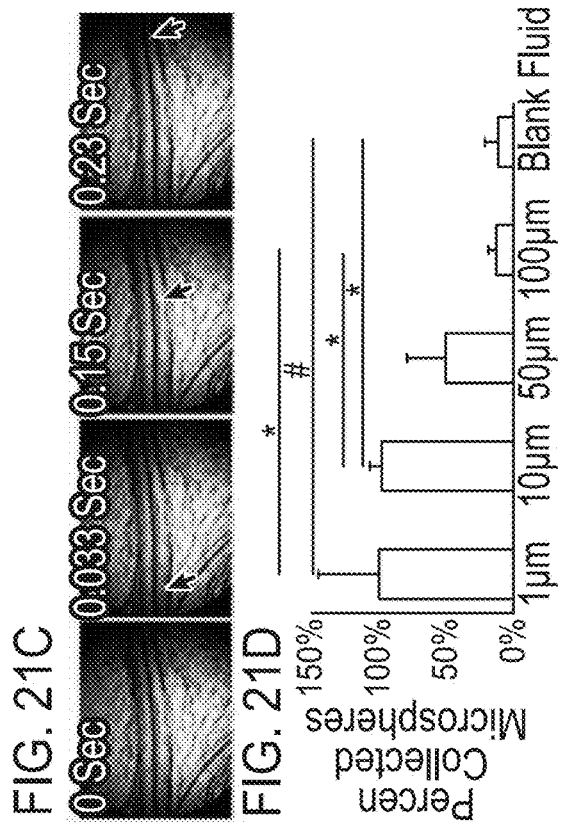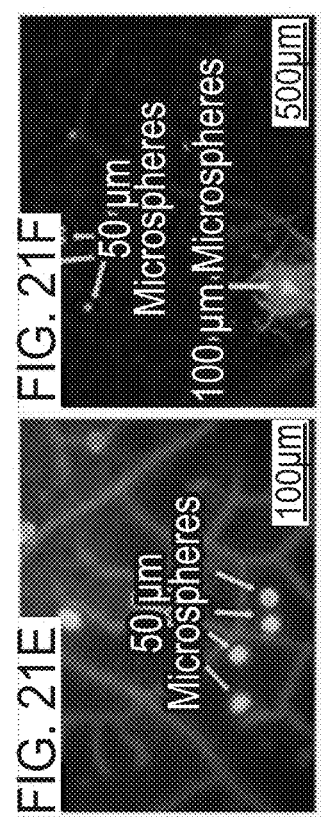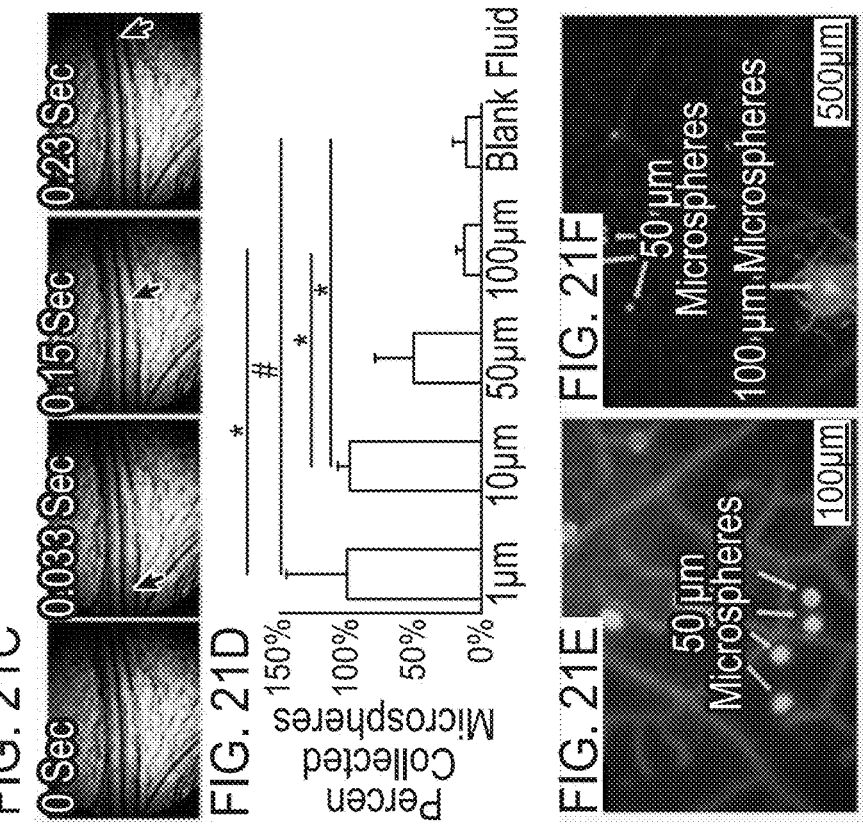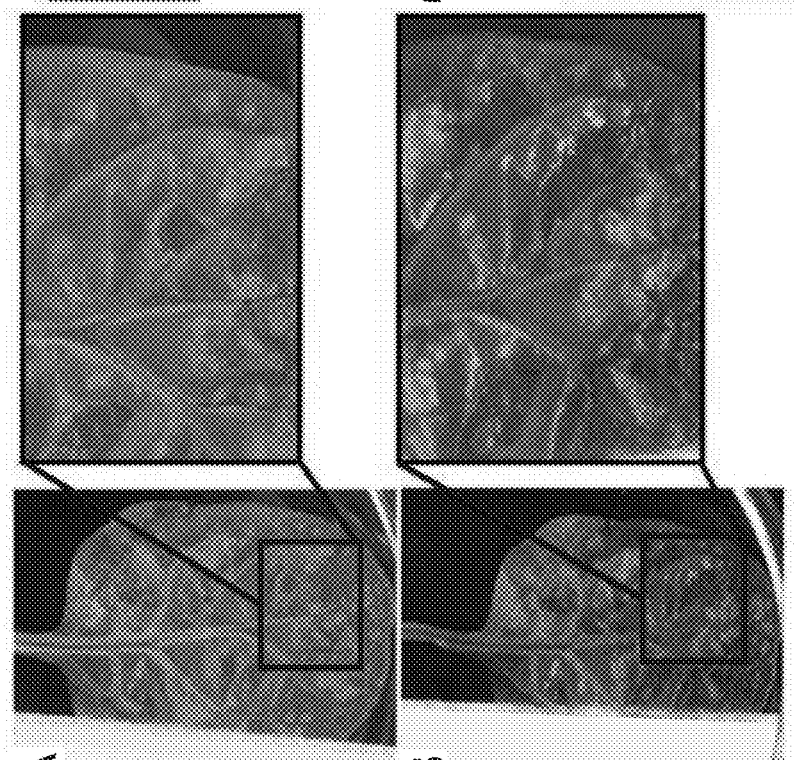

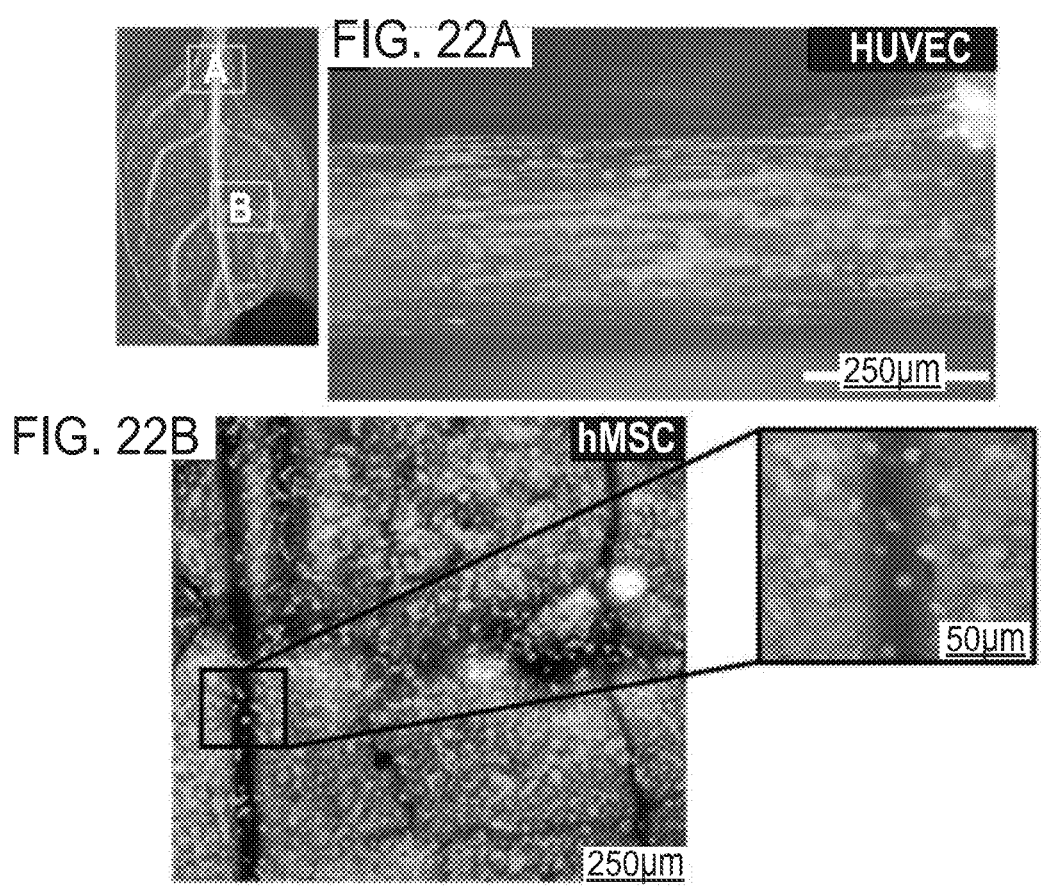

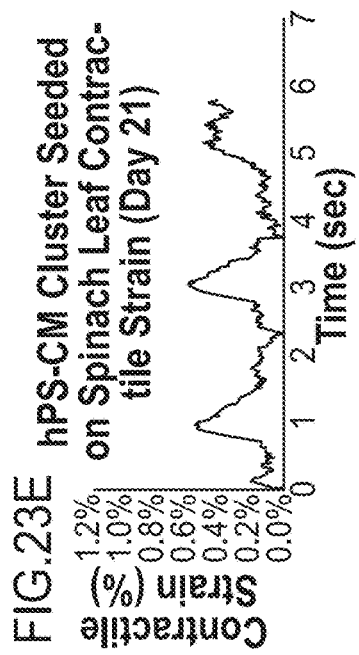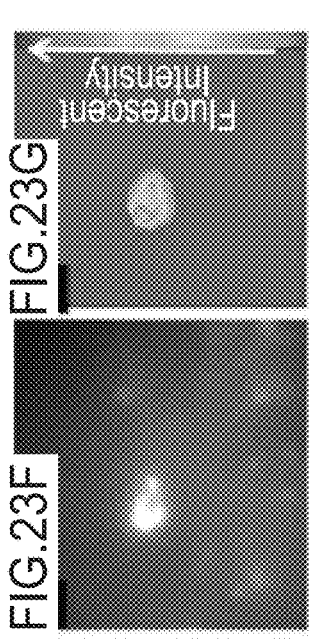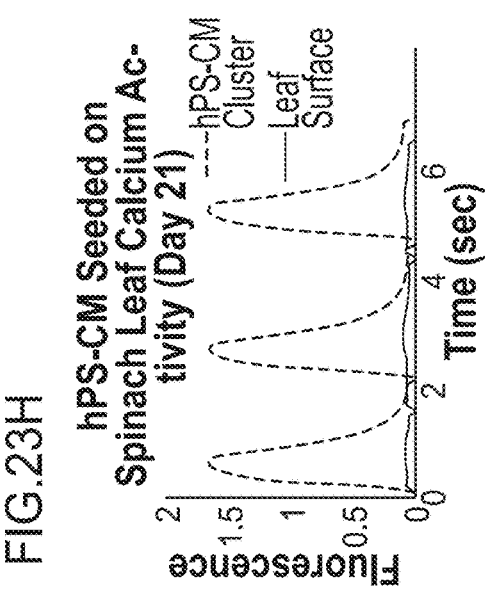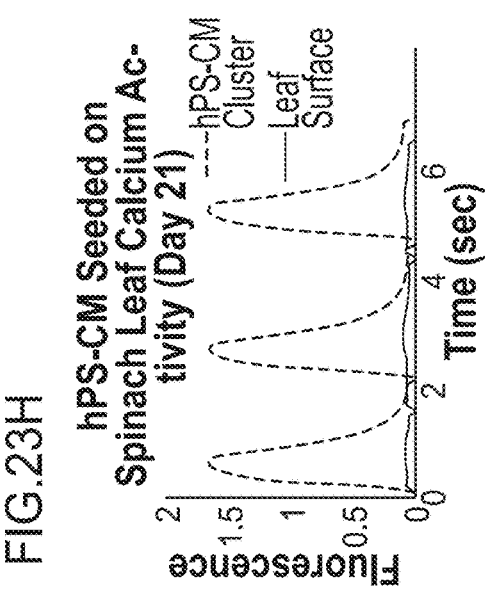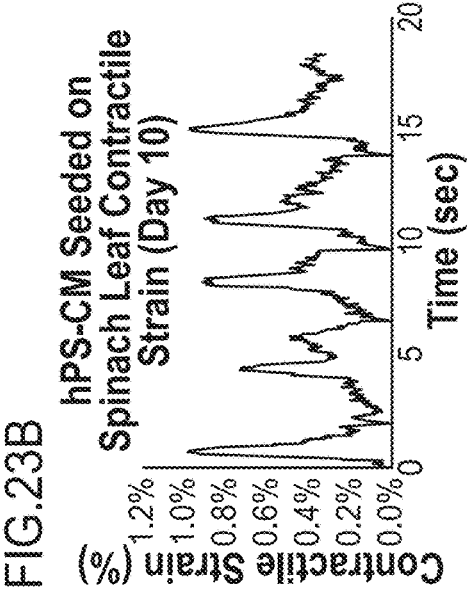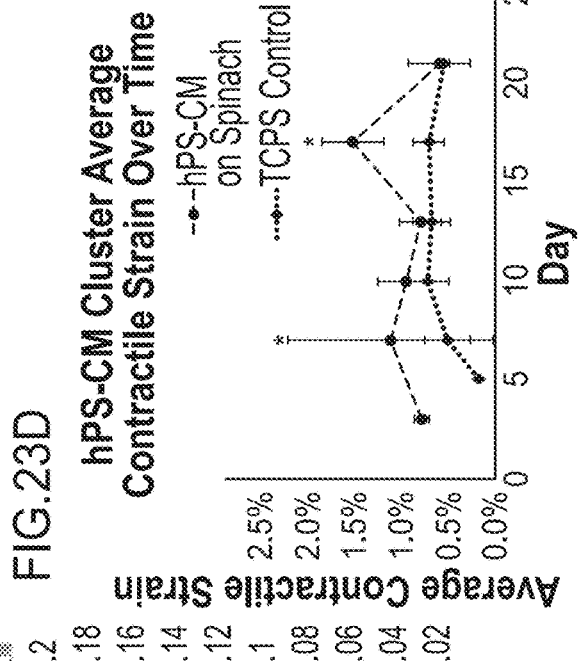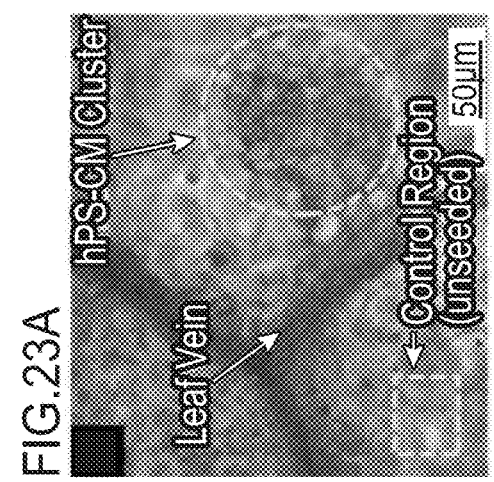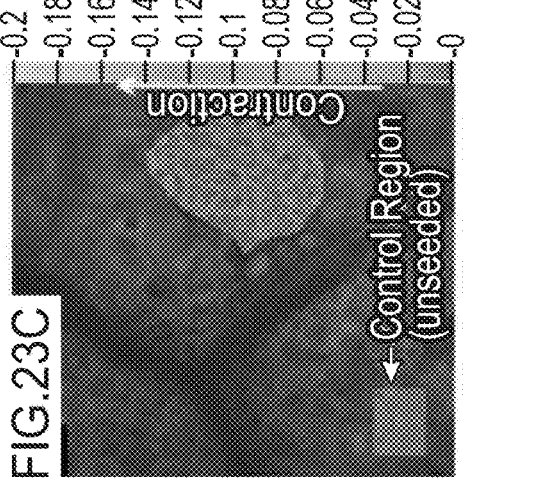

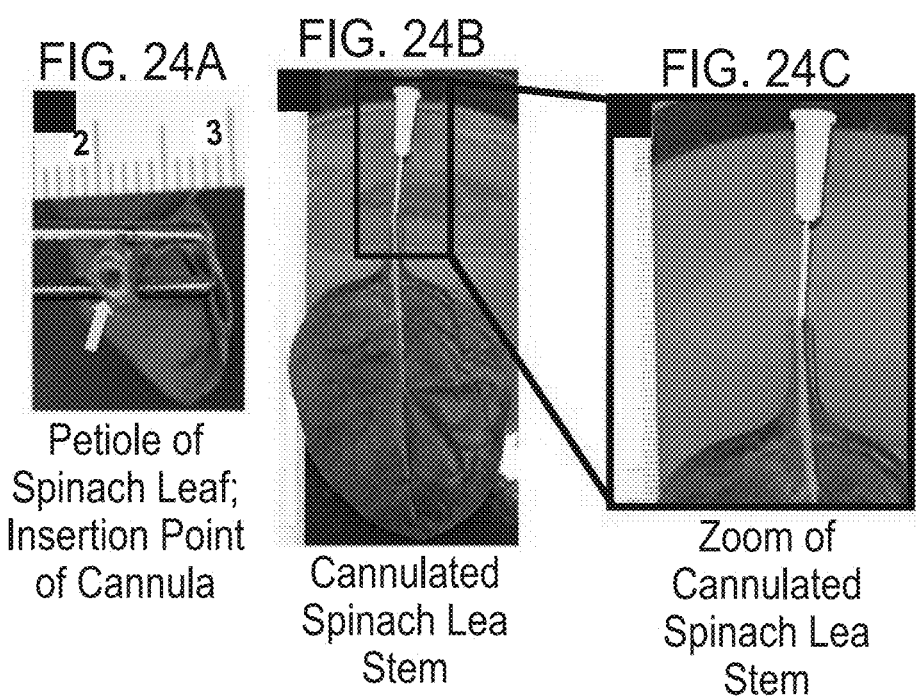

US 12,280,177 B2

SEQUENCE LISTING

```
<160> NUMBER OF SEQ ID NOS: 45

<210> SEQ ID NO 1
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: GAMMA-CARBOXYGLUTAMIC ACID HYDROXYLATION
<220> FEATURE:
<221> NAME/KEY: MOD_RES
<222> LOCATION: (5)..(5)
<223> OTHER INFORMATION: GAMMA-CARBOXYGLUTAMIC ACID HYDROXYLATION
<220> FEATURE:
<221> NAME/KEY: MOD_RES
<222> LOCATION: (8)..(8)
<223> OTHER INFORMATION: GAMMA-CARBOXYGLUTAMIC ACID HYDROXYLATION

<400> SEQUENCE: 1

Asx Glu Pro Arg Arg Glu Val Ala Glu Leu
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: GAMMA-CARBOXYGLUTAMIC ACID HYDROXYLATION
<220> FEATURE:
<221> NAME/KEY: MOD_RES
<222> LOCATION: (8)..(8)
<223> OTHER INFORMATION: GAMMA-CARBOXYGLUTAMIC ACID HYDROXYLATION

<400> SEQUENCE: 2

Glu Pro Arg Arg Ala Val Ala Glu Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
```

```
<223> OTHER INFORMATION: GAMMA-CARBOXYGLUTAMIC ACID HYDROXYLATION

<400> SEQUENCE: 3

Glu Pro Arg Arg Ala Val Ala Ala Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Glu Pro Arg Arg Glu Val Ala Glu Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Glu Pro Arg Arg Ala Val Ala Glu Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Glu Pro Arg Arg Ala Val Ala Ala Leu
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Arg Gly Asp Ser
1

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8

Cys Arg Gly Asp Ser
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic
```

<400> SEQUENCE: 9

Cys Arg Gly Asp Ser Pro
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Pro His Ser Arg Asn
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Gly Trp Gly Gly Arg Gly Asp Ser Pro
1               5

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Ser Ile Asp Gln Val Glu Pro Tyr Ser Ser Thr Ala Gln
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic

<400> SEQUENCE: 13

Gly Arg Asn Ile Ala Glu Ile Ile Lys Asp Ile
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Asp Ile Thr Tyr Val Arg Leu Lys Phe
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

```
<400> SEQUENCE: 15

Asp Ile Thr Val Thr Leu Asn Arg Leu
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Gly Arg Tyr Val Val Leu Pro Arg
1               5

<210> SEQ ID NO 17
<211> LENGTH: 13
<212> TYPE: PRT
<213> ORGANISM: Artificial Sequence
<220> FEATURE:
<223> OTHER INFORMATION: Synthetic

<400> SEQUENCE: 17

Gly Asn Arg Trp His Ser Ile Tyr Ile Thr Arg Phe Gly
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Gly Ala Ser Ile Lys Val Ala Val Ser Ala Asp Arg
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Gly Thr Thr Val Lys Tyr Ile Phe Arg
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic

<400> SEQUENCE: 20

Gly Ser Ile Lys Ile Arg Gly Thr Tyr Ser
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic

<400> SEQUENCE: 21
```

```
Gly Ser Ile Asn Asn Asn Arg
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Ser Asp Pro Gly Tyr Ile Gly Ser Arg
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic

<400> SEQUENCE: 23

Tyr Ile Gly Ser Arg
1               5

<210> SEQ ID NO 24
<211> LENGTH: 14
<212> TYPE: PRT
<213> ORGANISM: Artificial Sequence
<220> FEATURE:
<223> OTHER INFORMATION: Synthetic

<400> SEQUENCE: 24

Gly Thr Pro Gly Pro Gln Gly Ile Ala Gly Gln Gly Val Val
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic

<400> SEQUENCE: 25

Gly Thr Pro Gly Pro Gln Gly Ile Ala Gly Gln Arg Val Val
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Synthetic

<400> SEQUENCE: 26

Met Asn Tyr Tyr Ser Asn Ser
1               5

<210> SEQ ID NO 27
<211> LENGTH: 12
<212> TYPE: PRT
<213> ORGANISM: Artificial Sequence
<220> FEATURE:
<223> OTHER INFORMATION: Synthetic

<400> SEQUENCE: 27
```

```
Lys Lys Gln Arg Phe Arg His Arg Asn Arg Lys Gly
1               5                   10

<210> SEQ ID NO 28
<211> LENGTH: 22
<212> TYPE: PRT
<213> ORGANISM: Artificial Sequence
<220> FEATURE:
<223> OTHER INFORMATION: Synthetic

<400> SEQUENCE: 28

Cys Arg Gly Asp Gly Gly Gly Gly Gly Gly Gly Gly Gly Gly
1               5                   10                  15

Gly Pro His Ser Arg Asn
            20

<210> SEQ ID NO 29
<211> LENGTH: 19
<212> TYPE: PRT
<213> ORGANISM: Artificial Sequence
<220> FEATURE:
<223> OTHER INFORMATION: Synthetic

<400> SEQUENCE: 29

Cys Pro His Ser Arg Asn Ser Gly Ser Gly Ser Gly Ser Gly
1               5                   10                  15

Arg Gly Asp

<210> SEQ ID NO 30
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Acetylated

<400> SEQUENCE: 30

Gly Cys Tyr Gly Arg Gly Asp Ser Pro Gly
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Synthetic

<400> SEQUENCE: 31

Cys Arg Asp Gly Ser
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-amino acid

<400> SEQUENCE: 32

Arg Gly Asp Phe Cys
1               5
```

```
<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

Arg Lys Arg Leu Gln Val Gln Leu Ser Ile Arg Thr
1               5                   10

<210> SEQ ID NO 34
<211> LENGTH: 5
<212> TYPE: PRT
<213> ORGANISM: Artificial Sequence
<220> FEATURE:
<223> OTHER INFORMATION: Synthetic

<400> SEQUENCE: 34

Ile Lys Val Ala Val
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic

<400> SEQUENCE: 35

Tyr Ile Gly Ser Arg
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Lys Arg Thr Gly Gln Tyr Lys Leu
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic

<400> SEQUENCE: 37

Thr Tyr Arg Ser Arg Lys Tyr
1               5

<210> SEQ ID NO 38
<211> LENGTH: 17
<212> TYPE: PRT
<213> ORGANISM: Artificial Sequence
<220> FEATURE:
<223> OTHER INFORMATION: Synthetic

<400> SEQUENCE: 38

Lys Arg Thr Gly Gln Tyr Lys Leu Gly Ser Lys Thr Gly Pro Gly Gln
1               5                   10                  15
```

Lys

```
<210> SEQ ID NO 39
<211> LENGTH: 14
<212> TYPE: PRT
<213> ORGANISM: Artificial Sequence
<220> FEATURE:
<223> OTHER INFORMATION: Synthetic

<400> SEQUENCE: 39

Gln Ala Lys His Lys Gln Arg Lys Arg Leu Lys Ser Ser Cys
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Ser Pro Lys His His Ser Gln Arg Ala Arg Lys Lys Lys Asn Lys Asn
1               5                   10                  15

Cys

<210> SEQ ID NO 41
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = hydropathic residue
<220> FEATURE:
<221> NAME/KEY: MISC_FEATURE
<222> LOCATION: (2)..(3)
<223> OTHER INFORMATION: B = basic residue
<220> FEATURE:
<221> NAME/KEY: MISC_FEATURE
<222> LOCATION: (4)..(4)
<223> OTHER INFORMATION: X = hydropathic residue
<220> FEATURE:
<221> NAME/KEY: MISC_FEATURE
<222> LOCATION: (5)..(5)
<223> OTHER INFORMATION: B = basic residue
<220> FEATURE:
<221> NAME/KEY: MISC_FEATURE
<222> LOCATION: (6)..(6)
<223> OTHER INFORMATION: X = hydropathic residue

<400> SEQUENCE: 41

Xaa Asx Asx Xaa Asx Xaa
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = hydropathic residue
<220> FEATURE:
<221> NAME/KEY: MISC_FEATURE
<222> LOCATION: (2)..(4)
<223> OTHER INFORMATION: B = basic residue
<220> FEATURE:
```

```
<221> NAME/KEY: MISC_FEATURE
<222> LOCATION: (5)..(6)
<223> OTHER INFORMATION: X = hydropathic residue
<220> FEATURE:
<221> NAME/KEY: MISC_FEATURE
<222> LOCATION: (7)..(7)
<223> OTHER INFORMATION: B = basic residue
<220> FEATURE:
<221> NAME/KEY: MISC_FEATURE
<222> LOCATION: (8)..(8)
<223> OTHER INFORMATION: X = hydropathic residue

<400> SEQUENCE: 42

Xaa Asx Asx Asx Xaa Xaa Asx Xaa
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic

<400> SEQUENCE: 43

Arg Gly Asp Ser Pro
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gly Ser Gly Ser Gly Ser
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic

<400> SEQUENCE: 45

Arg Gly Asp Gly Gly Gly
1               5
```

FUNCTIONALIZATION OF PLANT TISSUES FOR HUMAN CELL EXPANSION

PRIORITY CLAIM

This application is a continuation application of U.S. application Ser. No. 16/085,220 (published as U.S. Publication No. 2019/0117839), filed Sep. 14, 2018, which is a national phase application of WO 2017/160862, filed Mar. 14, 2017, which claims priority to U.S. Provisional Application Ser. No. 62/307,771, filed Mar. 14, 2016; U.S. Provisional Application Ser. No. 62/318,953, filed Apr. 6, 2016; and U.S. Provisional Application Ser. No. 62/462,653, filed Feb. 23, 2017, each of which is incorporated by reference in its entirety.

STATEMENT OF GOVERNMENT SUPPORT

This invention was made with government support under HL093282 awarded by the National Institute of Health, 1144804 awarded by the National Science Foundation and RD-83573701-0 awarded by the Environmental Protection Agency. The government has certain rights in the invention.

INCORPORATION OF SEQUENCE LISTING

A paper copy of the Sequence Listing and a computer readable form of the Sequence Listing containing the file named "P160290US04_ST25.txt", which is 34,061 bytes in size (as measured in MICROSOFT WINDOWS® EXPLORER), are provided herein and are herein incorporated by reference. This Sequence Listing consists of SEQ ID NO:1-45.

BACKGROUND OF THE DISCLOSURE

The present disclosure relates generally to decellularized plant tissues and the use of these decellularized plant tissues as scaffolds for cell culture (e.g., cell expansion, cell differentiation, cell proliferation, cell growth, etc.). In some embodiments, the decellularized plant tissues are further functionalized such to allow for improved human cell adhesion, thereby allowing for their use as scaffolds for human cells. These scaffolds can then be used in a number of applications/markets, including as research tools for tissue engineering, regenerative medicine, and basic cellular biology.

Biomaterials are commonly used to provide scaffolding for biomedical applications, such as tissue engineering and cellular biomanufacturing. These scaffolds provide a critical framework for 3-dimensional cell growth and neo-tissue formation. The commercial success of tissue engineering products, such as scaffolds, requires not only efficacy, but also cost effectiveness. Unfortunately, even with the current technology, the production of biomaterials that bear high levels of structural complexity is still prohibitive from a cost-point of view. Moreover, the long periods of time required for design and optimization of biomaterials can significantly delay their implementation.

Further, despite the current technological advances, it remains challenging to manufacture materials with similar combinations of stiffness and toughness at low density and with elevated degree of pore interconnectivity. Particularly, the most desirable scaffolds including interconnected porosity for fluid transport, biochemical properties that support cell function, and a diversity of physical and mechanical properties that can be customized for specific biological or medical needs. Moreover, materials for tissue engineering are generally required to be highly hydrophilic and possibly made of natural polymers to decrease the likelihood of adverse responses in the body. An additional key challenge is the inability to incorporate a viable vascular networks into tissue engineered grafts. Conventional approaches encounter a 100-200 µm diffusion limit before the tissue engineered grafts become a viable clinical solution.

Recent advanced manufacturing approaches, such as 3-D printing or decellularization of animal tissues, have produced scaffolds with biomimetic or unique physical properties. Decellularization removes cellular material from a tissue or organ leaving behind an acellular scaffold consisting of extracellular matrix (ECM), the composition of which depends on the tissue or organ from which it was derived, while preserving an intact vascular network. By removing the cellular material of a donor's tissue, a decellularized graft would be rendered non-immunogenic while retaining gross organ structure. Decellularized tissues and organs can then be recellularized with cells. For example, when decellularized tissues and organs are decellularized with a patient's own cells, an autologous graft is prepared.

Native biochemical composition and hierarchical tissue structure of a potential decellularized graft are derived from the donor of the tissue or organ. This inherently leads to inconsistency among tissues or organs derived from different patients, or decellularized using different methods, due to confounding variables such as age, organism and/or tissue pathology, and the specifics of the decellularization protocol. Decellularized mammalian tissues are also in short supply and, even when available, are expensive.

Plants and animals exploit fundamentally different approaches to transporting fluids, chemicals, and macromolecules, yet there are surprising similarities in their vascular network structures. Plant vasculature follows Murray's Law, which is the physiological law describing the tapered, branching network design of the human cardiovascular system. Structures within the plant tissue, like human tissue, exhibit varied mechanical properties, enabling varied functions. Further, over 700 million years of evolution have developed plants with considerable diversity of properties that are often in defiance of the conundrum of materials that are both strong and tough. Plant materials also offer unique transport properties, as hydraulic conductance in plants is achieved by the branching of wide conduits into smaller vessels. Transpiration of water from the leaves creates a negative pressure that generates the motive force for the ascent of sap. This energy-efficient mechanism is possible because plant structures are designed to include highly interconnected pores and vessels to maintain hydraulic continuity and allow the propagation of the negative pressure generated in the leaves.

It was found; however, that in some cases animal cells, and in particular, human cells interact very poorly with plant tissues. Particularly, the cells do not effectively adhere to decellularized plant tissues. It would, therefore, be advantageous, in some embodiments, if the decellularized plant tissues could be manipulated such to enable human cell adhesion.

BRIEF DESCRIPTION OF THE DISCLOSURE

The present disclosure is generally related to decellularized plant tissues and the use of these decellularized plant tissues as scaffolds for cell culture. In particularly suitable embodiments, the decellularized plant tissues are functionalized using one or two methods according to the present disclosure. In the first method, the decellularized plant tissue is functionalized by incubating the tissue in a modified simulated body fluid (SBF) to form a mineral layer on the decellularized plant tissue. In the second method, the decellularized plant tissue is decorated with adhesive molecules, particularly, with a plant adhesion molecule conjugated to a cell adhesion peptide, to functionalize the decellularized plant tissue. Such functionalization allows for improved cell adhesion to the plant tissue, thereby allowing for their use as scaffolds for cell maturation, expansion, proliferation, differentiation, and formation of cellular structures (e.g., tubules).

Accordingly, in one aspect, the present disclosure is directed to a plant scaffold comprising a decellularized plant tissue comprising a plant adhesion molecule conjugated to a cell adhesion peptide. In another aspect, the present disclosure is directed to a cell culture method comprising contacting a cell with the plant scaffold as set forth above.

In another aspect, the present disclosure is directed to a plant scaffold comprising a decellularized plant tissue and a mineral layer. In another aspect, the present disclosure is directed to a cell culture method comprising contacting a cell with the plant scaffold as set forth above.

In yet another aspect, the present disclosure is directed to a method for preparing a plant scaffold for tissue engineering. The method comprises: decellularizing a plant tissue; coating the decellularized plant tissue with a plant adhesion molecule conjugated to a cell adhesion peptide.

In another aspect, the present disclosure is directed to a method for preparing a plant scaffold for tissue engineering. The method comprises: decellularizing a plant tissue; submerging the decellularized plant tissue in a modified simulated body fluid solution to form a mineral layer on the decellularized plant tissue. The deposited mineral layer comprises predominantly calcium carbonate, phosphate, magnesium and potassium.

In yet another aspect, the present disclosure is directed to a method of engineering mammalian tissue, the method comprising: decellularizing a plant tissue to provide a plant scaffold having a perfusable structure; and culturing a cell within the plant scaffold.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1A is an illustration of plant tissue processing. The cellular component of plant stems or leaves was eliminated by immersion in a series of detergents and bleach. Plant tissues were then biofunctionalized to provide a substrate for adhesion of human cells, using either biomineralization or coating with dopamine-conjugated RGD peptides (RGDOPA). FIG. 1B depicts DNA quantification in parsley stems, measured using the CYQUANT® assay, showing a marked decrease in DNA content after decellularization. (*) represents statistically significant differences using paired student's t-test n=3, $p<0.05$. FIG. 1C depicts images displaying the different appearance between normal and decellularized parsley stems. Color-enhanced SEM micrographs highlight the presence of a waxy cuticle on the surface of normal parsley stems, while the immersion in a hexane bath during the decellularization process dissolved the hydrophobic waxy layer and left a grooved surface structure.

FIGS. 2A-2G depict that the histology characterization reveals effective decellularization. Sass's Safranin-O (it stains nuclei and chromosomes red) and Fast Green (it stains cytoplasms and cell walls bright green) staining of sections of plant tissues show effective decellularization of plant stems. FIG. 2A depicts a section of normal parsley. FIG. 2B depicts a section of decellularized parsley stem. FIG. 2C depicts a section of decellularized *Anthurium waroqueanum* stem. FIG. 2D depicts a section of orchid's pseudobulb. FIG. 2E depicts a section of *Calathea zebrina* stem. FIG. 2F depicts a section of *Solenostemon* stem. FIG. 2G depicts a section of Vanilla stem. Scale bars 500 μm and 50 μm in the magnified images.

FIGS. 3A-3N show that plant's stems maintain high porosity after decellularization. FIGS. 3A-3L depict paired SEM micrographs of plant stems before (left) and after (right) decellularization: (FIGS. 3A & 3B) Bamboo, (FIGS. 3C & 3D) *Anthurium waroqueanum*, (FIGS. 3E & 3F) *Calathea zebrina*, (FIGS. 3G & 3H) Orchid's pseudobulb, (FIGS. 3I & 3J) Parsley, (FIGS. 3K & 3L) Vanilla. The inset photographs show the visual appearance of decellularized plants after decellularization. FIG. 3N shows a comparison of average pore size before and after decellularization of stems. Differences were assessed using a paired t-test; $p<0.05$. The robust regression and outlier removal (ROUT) method was used to identify outliers using the software GraphPad Prism.

FIGS. 4A-4E depicts a comparison of structural changes before and decellularization. FIGS. 4A & 4B depict SEM cross-sections of bamboo stems respectively before and after decellularization. No major structural changes occurred and the pores size in both stems was comparable. FIGS. 4C & 4D depict SEM cross-sections of parsley stems before and after decellularization respectively. In this case, pores diameter was significantly enlarged in decellularized stems. FIG. 4E depicts a 3D representation of pores depth in a *Anthurium waroqueanum* stem. The total length of the stem was 7 mm and the deepest pore measured about 3 mm in depth. Imaging performed using the digital microscope VHX-5000 by Keyence.

FIG. 5A depicts a HPLC spectra of the peptide RGDGGG showing a single major peak indicative of high purity. The elution time for the peptide alone was 7.53 minutes. FIG. 5B depicts a HPLC spectra of the peptide RGDGGG conjugated with dopamine (RGDOPA). Following dialysis there appears to be only minimal presence of un-conjugated peptide and the elution time of the main peak is 8.47 minutes, a shift of about 1 minute relative to the un-conjugated peptide.

FIG. 5F shows a Parsley stem functionalized with FITC-RGD, scalebars 100 μm; FIG. 5G shows a Parsley stem functionalized with FITC-RGDOPA, scalebars 100 µm; FIG. 5H shows the quantification of the total peptide bound to different stems after 16 hours of incubation; FIG. 5I is a comparison of loading kinetics of FITC-RGD and FITC-RGDOPA. The peptide conjugation to dopamine increases significantly its ability to bind to the plant stems. FIGS. 5J-5N depicts FITC-RGDOPA loading kinetics respectively on, bamboo, *Calathea zebrina*, orchid's pseudobulbs, *Anthurium waroqueanum*, and vanilla stems.

FIGS. 6A-6I depict biofunctionalized plants as scaffolds for human cells. FIG. 6A depicts rhodamine-phalloidine staining of actin filaments (red) and dapi staining of nuclei (blue) of hDFs cultured for 2 days in ultralow attachment polystyrene wells (scale bars 500 µm). FIG. 6B depicts color-enhanced SEM micrographs displaying hDFs (orange) adhering on a biomineralized parsley stem (blue). FIG. 6C depicts rhodamine-phalloidin and DAPI staining of hDFs cultured for 2 days on RGDOPA-coated ultralow attachment polystyrene well (scale bars 500 µm). FIGS. 6D-6F depict calcein staining of hDFs seeded on decellularized parsley stems untreated (FIG. 6D), biomineralized (FIG. 6E), and coated with RGDOPA (FIG. 6F) (scale bars 100 µm). The images show selective cell adhesion on functionalized surfaces. FIG. 6G depicts a decellularized parsley stem following 7 days incubation in mSBF showing growth of a mineral coating with spheroidal morphology within the pores of the stem. The smallest pores appear to be occluded by the mineral, but larger pores and vascular bundles are open and morphological features are maintained after the mineralization. FIGS. 6H & 6I depict SEM micrographs of decellularized stems coated with RGDOPA. A cross-section of a *Calathea zebrina* stem (FIG. 6H) shows that the RGDOPA coating does not occlude even the smallest (~2 µm) pores; a side-view of a vanilla stem (FIG. 6I) shows that the topographical cues of the stems are still evident after the RGDOPA coating.

FIGS. 7A-7C depict calcein staining of hDF cultured for 2 days on *Impatiens capensis* stems respectively: non treated (FIG. 7A), RGDOPA-coated (FIG. 7B) and RGDOPA-coated and cultured for 2 weeks (FIG. 7C). When seeded on treated stems, cells acquired the typical spindle-shape of adhering cells, while, when seeded on non-treated stems, they were rounded, the hallmark of low interaction with the surface of plant tissues. After 2 weeks of culture (FIG. 7C) there were visibly more cells on the stem compared to 2 days (FIG. 7B) indicating cell expansion. Scale bars 250 µm. FIG. 7D depicts rhodamine-phalloidine staining of actin filaments (red) and dapi staining of nuclei (blue) of hDF cultured on *Impatiens capensis* stems for 2 weeks. Scale bar 250 µm. FIGS. 7E & 7F show color-enhanced SEM micrographs displaying hDF (pink) growing on the surface of *Impatiens capensis* stems (green).

FIGS. 8A-8E depict the effects of mineralization on parsley stems: FIGS. 8A-8B, SEM micrograph and EDS analysis of a parsley stem non-mineralized (FIG. 8A) and mineralized (FIG. 8B). FIGS. 8C-8E, mechanical testing revealed that mineralization of parsley stems increased their young's modulus (FIG. 8C) but it did not have significative effects on their strain at failure (FIG. 8D) or tensile stress (FIG. 8E).

FIGS. 9A-9F depict the mineralization of plant's stems. FIG. 9A depict a mineralized parsley stem. FIGS. 9B & 9C depict SEM micrographs comparing the surface of mineralized and non-mineralized parsley stems respectively. The surface of mineralized parsley stems is characterized by the presence of mineral flakes, normal parsley instead, shows smoother surfaces typical of cuticle tissue. FIGS. 9D & 9E depict SEM micrographs comparing the surface of mineralized and non-mineralized bamboo stems. Mineral-coated bamboo stems display rough surfaces, normal bamboo instead show very smooth surfaces. FIG. 9F depicts faxitron images of respectively coated and non-coated bamboo stems.

FIGS. 10A-10F depict calcein staining of hDF seeded on different stems: Calcein staining of hDF cultured for 7 days on a variety of RGDOPA-coated stems show that cells were able to adhere and be viable on all plant scaffolds. Cells were seeded respectively on: FIG. 10A, Solenostemon. FIG. 10B, *Anthurium waroqueanum*. FIG. 10C, Bamboo. FIG. 10D, Orchid's pseudobulb. FIG. 10E, Vanilla. FIG. 10F, Parsley. Scale bars 250 µm.

FIGS. 11A-11L depict expansion of human cells on decellularized plant stems. FIGS. 11A & 11B show the metabolic activity of cells as measured using the CELLTITER-BLUE® assay. MSCs (FIG. 11A) show a steady increase in metabolic activity only on monolayer and on parsley stems, and they decrease in other plant stems. Similar behavior was observed also in hDF (FIG. 11B), however, in this case there was a significant increase in metabolic activity also in orchid's pseudobulb stems. n=3, p<0.05 paired student's t-test. FIGS. 11C & 11D show the quantification of total DNA content assessed using the PICOGREEN® assay and compared between day 1 and day 50 of culture, n=3, p<0.05 paired student's t-test. FIGS. 11E & 11F depict the DNA content (ng/mm$^2$) normalized by seeding area; n=3, p<0.05 paired student's t-test. FIGS. 11G & 11H depict the Orchid's pseudobulb and a mineralized parsley stem respectively in ultralow attachment polystyrene wells. They clearly have different volumes and offer different cell seeding areas. FIG. 11I depicts tropical *Anthurium magnificum* leaf before and after decellularization. The leaves of *Anthurium magnificum* are on average 30 cm wide and 40 cm long, in the images their size is directly compared to that of a human hand. Scale bar 15 cm. FIG. 11J depicts a decellularized *Anthurium magnificum* leaf cut using 8 mm biopsy punch and used as scaffold for culture of HUVEC cells. After 5 days of culture, live cells were stained using calcein (green). FIGS. 11K & 11L depict rhodamine-phalloidin staining (FIG. 11K) of actin filaments (red) and DAPI staining of nuclei (blue) and relative brightfield image (FIG. 11L) of HUVEC cells cultured on the decellularized *Anthurium magnificum* leaf for 5 days. The brightfield image (FIG. 11L) displays the presence of vascular structures and cells appear to register the shape of the vessels (FIG. 11K). From a single leaf of *Anthurium magnificum* it was possible to obtain numerous pre-vascularized scaffolds. Scale bars 100 µm.

FIGS. 12A-12O shows that cell orientation follows the plant's topographical cues. FIG. 12A depicts an illustration of the method used for the quantification of orientation angle (OA) between the mammalian cell and the underlying plant structure. FIG. 12B shows that only 15% of the cells seeded on monolayer had an OA<20°, whereas more than 40% of the cells seeded on Solenostemon were aligned with the stem's topography(OA<20°). n=3, p<0.05, One-way ANOVA followed by Dunnett's multiple comparisons test. FIGS. 12C-12F depict rhodamine-phalloidin staining of actin filaments (red) and DAPI staining of nuclei (blue) of hDFs cultured on monolayer (FIG. 12C), Solenostemon (FIG. 12D), Parsley (FIG. 12E), and Vanilla leaves (FIG. 12F), scale bars 100 µm. Cells appear to follow the topographical cues of each of the plant tissues. FIG. 12G depict a color-enhanced SEM micrograph of hDFs seeded on parsley stems showing that cells grow preferably in the concave areas of the plant tissues. FIG. 12H is a SEM micrograph displaying the surface topography of an *Anthurium waroqueanum* stem. FIG. 12I depicts hDF seeded on *Anthurium* stems that conform into a pattern reminiscent of the plant topography. Actin filaments were stained red with Rhodamine-phalloidine nuclei stained blue with dapi. FIG. 12J depicts a color-enhanced SEM micrograph displaying a hDF cell adhering on the surface of a summer lilac leaf. FIG. 12K depicts a SEM micrograph showing a cross-section of a *Schoenoplectus tabernaemontani* stem. FIG. 12L shows DAPI staining of hDF cultured on a *Schoenoplectus tabernaemontani* stem for 30 days. Scale bar 250 µm. FIG. 12M is a Brightfield image of a summer lilac leaf after decellularization. The decellularization protocol allowed for maintenance of the vasculature of the leaf. FIGS. 12N-12O depict hDF seeded on a summer lilac leaf and live-stained with calcein (FIG. 12N) or stained using rhodamine-phalloidine, DAPI (FIG. 12O). Cells were expanded on the leaves for 4 days, and during this period they populated the entire leaf and grew around the vasculature, thereby using the leaf's structure as a template. Scale bars 250 µm.

FIG. 13A is a SEM micrograph showing a sideview of a *Schoenoplectus tabernaemontani* stem. This plant appears to have several internal layers that increase its surface area and maximize the plant's ability to exchange oxygen and nutrients. FIG. 13B is a SEM micrograph displaying hDF seeded in a *Schoenoplectus tabernaemontani* stem. The high surface area of this stem may allow considerable cell expansion. FIGS. 13C & 13D depict color-enhanced SEM micrographs of hDF seeded respectively on a summer lilac leaf (FIG. 13C) and on Solenostemon stems (FIG. 13D).

FIGS. 14A-14L show the interplay between hDF and structural cues of parsley stems: FIG. 14A depicts rhodamine-phalloidine staining of actin filaments (red) and dapi staining of nuclei (blue) of hDF seeded on parsley stems. Cells appeared to be polarized, following the topographical orientation of the stem. FIG. 14B depicts calcein live-staining of hDF seeded on parsley stems for 7 days. Scale bars 250 µm. FIG. 14C depicts a color-enhanced SEM micrograph of hDF cultured on parsley stems. Cells seemed to grow in the proximity of concave areas of the stem. FIGS. 14D-14K depict a panel of SEM images showing a number of cases in which hDF (highlighted with red arrows) were found in proximity of the stomata on parsley stems. FIG. 14L is a SEM micrograph showing hDF adhering on concave areas on a parsley stem.

FIG. 15A is an illustration of the method used for the quantification of OA. In the case of plant tissues, an axis was drawn following the topography of the stems and the software cellProfiler was used to measure the angle between the longest side of the cell's nuclei and the axis. Only cells oriented within certain angle ranges were counted and normalized over the total number of cells. FIGS. 15B-15E depict the quantification of cellular orientation respectively on monolayer (FIG. 15B), Solenostemon (FIG. 15C), Parsley (FIG. 15D) and Vanilla leaf (FIG. 15E). Clearly, the data show that increasing the angle range corresponds to an increase of percentage of cells oriented in the same direction. Using a range of 40 degrees, it was found that 30% of the cells are oriented the same way in monolayer, 75% in Solenostemon, 50% in Parsley and 50% in Vanilla leaf. Monolayer (750 cells, 3 samples), Solenostemon (1792 cells, 4 samples), Parsley (617 cells, 4 samples), Vanilla leaves (864 cells, 3 samples) $p<0.05$ one-way ANOVA followed by Tukey's multiple comparisons test. FIGS. 15F & 15G depict the quantification of cellular orientation comparing samples with one another. Regardless of the angle range considered, significantly more cells follow the same orientation in Solenostemon, Parsley and Vanilla leaves compared to the monolayer control. $n=3$, $p<0.05$, One-way ANOVA followed by Dunnett's multiple comparisons test.

FIGS. 16A-16C, SEM micrographs of respectively the surface (FIG. 16A), a side-view (FIG. 16B) and a cross-section (FIG. 16C) of solenostemon stems. FIGS. 16D-16E, Rhodamine-phalloidine staining of actin filaments (red) and dapi staining of nuclei (blue) of hDF growing respectively on the surface (FIG. 16D) or within (FIG. 16E) solenostemon stems. Cells growing on the stem's surface appeared to have a random orientation (FIG. 16D) while cells growing within the stem (FIG. 16E) seemed to align to the stem's topography. Scalebars 250 µm.

FIGS. 19A-19D depicts the decellularization process as used in one embodiment of the present disclosure.

FIGS. 20A-20F & 20I-20K depict decellularized plant tissue by light microscopy (FIGS. 20A-20D) and by electron microscopy (FIGS. 20E-20F & 20I-20K).

FIG. 20G depict DNA per amount of tissue in plant tissue and decellularized plant tissue.

FIG. 20H depict protein per amount of tissue in plant tissue and decelluaIrized plant tissue.

FIGS. 21A & 21B depict that plant vasculature remains after decellularization.

FIGS. 21C-21F depict fluorescent microsphere perfusion.

FIGS. 22A & 22B depict recellularization of decellularized plant tissue with human cells.

FIGS. 23A-23H depict the functionality of human cells recellularized on decellularized plant tissue.

FIGS. 24A-24C depict a cannulated spinach leaf stem.

DETAILED DESCRIPTION

Figure 1A:
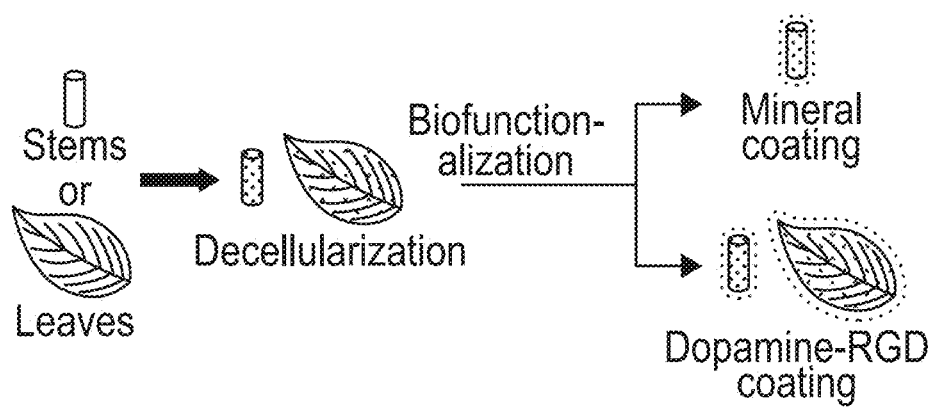
FIGS. 1A-1C depict decellularization of plant tissues.
Figure 1B:
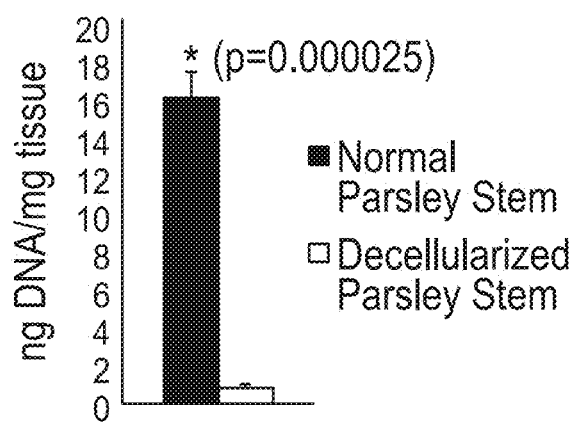
Figure 1C:
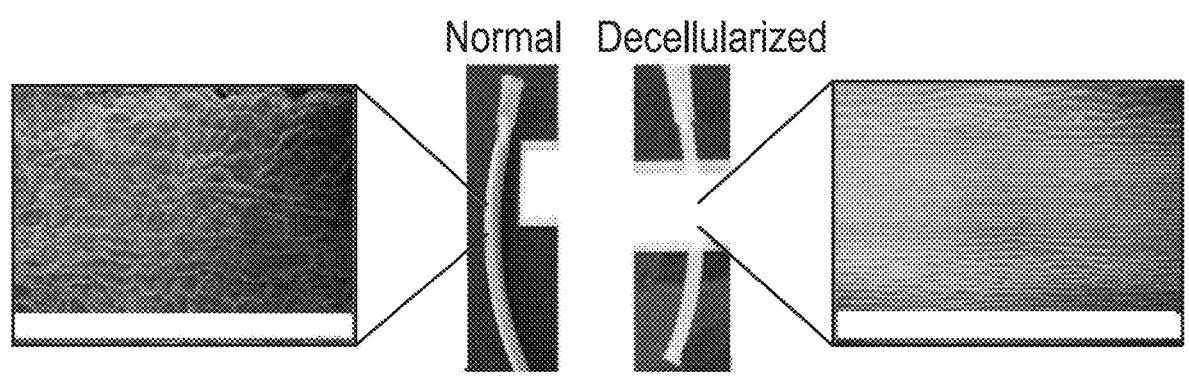

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The present disclosure is generally directed to decellularized plant tissues, and use of the tissues as scaffolds for cellular maturation, expansion, proliferation, differentiation, and formation of cellular structures (e.g., tubules). Additionally, in particularly embodiments, decellularized plant tissues can be further functionalized such to allow for cell adhesion, thereby allowing the use of the functionalized, decellularized plant tissues to be used as scaffolds for cells. While described fully herein with respect to human cells, it should be understood that any animal cells can be used with the decellularized (and, optionally, functionalized) plant tissues without departing from the scope of the present disclosure.

It has been found herein that the decellularized plant tissues can be used as adaptable scaffolds for culture of cells. The elevated hydrophilicity and excellent water transport abilities of plant tissues allow for cell expansion over prolonged periods of culture. Moreover, cells are able to conform to the microstructure of the plant frameworks, resulting in cell alignment and pattern registration.

Generally, any plant tissue suitable for decellularization as known in the art is suitable as a source for plant tissue in the methods of the present disclosure. For example, the plant tissue can include leaf tissue, stem tissue, root tissue, and combinations thereof. Further, any plants known in the art can be used. Without being limiting, exemplary plants include, without being limiting, spinach, sweet wormwood, parsley, vanilla, and peanut, and combinations thereof.

Initially, the plant tissues are first decellularized to eliminate compatibility issues. In some embodiments, the decellularized plant tissues are then functionalized. Particularly, the decellularization process allows for removal of cellular material from a tissue or organ leaving behind an acellular scaffold consisting of extracellular matrix (ECM), the composition of which depends on the tissue or organ from which it was derived (i.e., plant tissue), while preserving an intact vascular network.

Generally, the plant tissue is decellularized using any methods known in the art for decellularizing tissue. In one embodiment, the plant tissue is decellularized via detergent perfusion using at least one of a detergent and enzyme. Exemplary perfusion methods include immersion in detergents and bleaching agents such as sodium hypochlorite (bleach), sodium dodecyl sulfate, ethylenediaminetetraacetic acid (EDTA), Triton X-100, and the like, and combinations thereof. Exemplary enzymes for use in decellularization include lipases, thermolysin, galactosidases, nucleases (e.g., endonucleases such as benzoase), trypsin and combinations thereof. In some embodiments, the plant tissue can be decellularized using a mixture of detergent and enzyme, such as a mixture of EDTA and trypsin.

In particularly suitable embodiments, once decellularized, the decellularized plant tissue can then be functionalized (also referred to herein as "biofunctionalized") to allow for more effective adhesion of the plant tissues to cells, particularly human cells. With the functionalization techniques described herein, it is possible to enable adhesion of cells on a diverse set of plant tissues In one embodiment, the decellularized plant tissue is functionalized by mineralization of the plant tissue. More particularly, the decellularized plant tissue is incubated in a modified simulated body fluid (mSBF) to form a mineral layer coating on the surface of the decellularized plant tissue. In some embodiments, the decellularized plant tissue is incubated in mSBF for a period of from about 7 to about 14 days with gentle agitation. Suitable mSBF contains a suitable mineral-forming material to form the mineral layer. Suitable mineral-forming materials may be, for example, calcium, phosphate, carbonate, and combinations thereof.

The modified simulated body fluid (mSBF) for use in forming the mineral layer typically includes from about 5 mM to about 12.5 mM calcium ions, including from about 5 mM to about 10 mM calcium ions, and including about 5 mM calcium ions; from about 2 mM to about 12.5 mM phosphate ions, including from about 2 mM to about 7 mM phosphate ions, and including about 2 mM phosphate ions; and from about 4 mM to about 150 mM carbonate ions, and including about 150 mM carbonate ions.

The resulting deposited mineral layer generally predominantly includes calcium carbonate, phosphate, magnesium and potassium. In some particularly suitable embodiments, the resulting mineral layer includes calcium and phosphate in a calcium to phosphate ratio of from about 2.5:1 to about 1:1.

The pH of the resulting mineral layer may typically range from about 4 to about 7.5, including from about 5.3 to about 6.8, including from about 5.7 to about 6.8, and including about 6.8.

In some embodiments, the mineral layer for mineralization of the decellularized plant tissue may further include a mineral binding peptide to allow improved binding of cells and inclusion of growth factors with the functionalized, decellularized plant scaffold.

The mineral binding peptide (e.g., SEQ ID NO:1) typically includes an amino acid sequence inspired by the 5.7 kDa native protein osteocalcin (OCN), which contains three γ-carboxylated glutamic acid (Gla) residues at positions 1, 5, and 8 that coordinate with calcium ions (such as in the present mineral layers). Alternatively, it has been found that at least one or all three Gla residues present in SEQ ID NO:1 can be substituted with either glutamic acid (Glu) or alanine (Ala). Specifically, in some embodiments, the peptide sequences of SEQ ID NO:2 (γ-carboxylated glutamic acid (Gla) residues at positions 1 and 8 and Ala residue at position 5); SEQ ID NO:3 (γ-carboxylated glutamic acid (Gla) residue at position 1 and Ala residues at positions 5 and 8); SEQ ID NO:4 (Glu residues at positions 1, 5, and 8); SEQ ID NO:5 (Glu residues at positions 1 and 8 and Ala residue at position 5); and SEQ ID NO:6 (Glu residue at position 1 and Ala residues at positions 5 and 8) may be used as the hydroxyapatite-binding portion (see Table 1). The Glu and Ala substitutions can influence the charge density and secondary structure of the peptide molecules, and therefore, influence the binding.

TABLE 1

Exemplary Mineral Binding Peptide Sequences

| SEQ ID NO | Peptide | Amino Acid Sequence |
|---|---|---|
| 1 | γ-carboxylated glutamic acid (Gla) residues at positions 1, 5, and 8 | γEPRRγEVAγEL |
| 2 | γ-carboxylated glutamic acid (Gla) residues at positions 1 and 8 and Ala residue at position 5 | γEPRRAVAγEL |
| 3 | γ-carboxylated glutamic acid (Gla) residues at position 1 and Ala residues at positions 5 and 8 | γEPRRAVAAL |
| 4 | Glu residues at positions 1, 5, and 8 | EPRREVAEL |
| 5 | Glu residues at positions 1 and 8 and Ala residue at position 5 | EPRRAVAEL |
| 6 | Glu residue at position 1 and Ala residues at positions 5 and 8 | EPRRAVAAL |

In some embodiments, the mineral layer for mineralization of the decellularized plant tissue may further include a biomolecule that are suspected of binding or interacting with a cell to affect cell attachment, spreading, migration, maturation, expansion, proliferation, differentiation, and formation of cellular structures (e.g., tubules). Particularly suitable biomolecules can be nucleic acids, proteins, peptides, growth factors, proteoglycans, and combinations thereof. Suitable growth factors can be, for example, bone morphogenic protein, fibroblast growth factor, growth differentiation factor, platelet-derived growth factor, placental growth factor, transforming growth factor, insulin-like growth factor, vascular endothelial growth factor, bone sialoprotein, phosphorin, osteonectin and combinations thereof. More particularly suitable growth factors can be, for example, vascular endothelial growth factor, bone morphogenetic proteins, fibroblast growth factor, insulin-like growth factor and combinations thereof. Suitable proteoglycans and be, for example, proteoglycans with heparin, heparin sulfate, and/or chondroitin glycosaminoglycan side chains.

In another embodiment, the decellularized plant tissue is functionalized by decorating the decellularized plant tissue with adhesive cues such to allow adhesion of cells to the decellularized plant tissue. Particularly, the decellularized plant tissue can be contacted and/or coated with a plant adhesion molecule pre-conjugated to a cell adhesion peptide. Particularly, it was found that decellularized plant tissues that were coated with cell adhesion peptides pre-conjugated to plant adhesion molecules allowed for effective cell adhesion, even enabling human cell adhesion on plant tissues.

Suitable plant adhesion molecules include dopamine-containing compounds (including polydopamines), polyphenols and combinations thereof. Dopamine is a catechol moiety found in adhesive proteins and is capable of strong adhesion in aqueous environments. Without being limiting, exemplary dopamine-containing compounds include dopamine hydrochloride.

The plant adhesion protein is conjugated with a cell adhesive peptide prior to coating the decellularized plant tissue. As used herein, a "cell adhesion peptide" refers to an amino acid sequence obtained from an adhesion protein to which cells bind via a receptor-ligand interaction. Varying the cell adhesion peptide and concentrations thereof in the solution allow for the ability to control the stability of the cellular attachment to the resulting functionalized, decellularized plant scaffold. Suitable cell adhesion peptides include, for example, RGD, RGDS (SEQ ID NO:7), CRGDS (SEQ ID NO:8), CRGDSP (SEQ ID NO:9), PHSRN (SEQ ID NO:10), GWGGRGDSP (SEQ ID NO:11), SIDQVEPYSSTAQ (SEQ ID NO:12), GRNIAEIIKDI (SEQ ID NO:13), DITYVRLKF (SEQ ID NO:14), DITVTLNRL (SEQ ID NO:15), GRYVVLPR (SEQ ID NO:16), GNRWHSIYITRFG (SEQ ID NO:17), GASIKVAVSADR (SEQ ID NO:18), GTTVKYIFR (SEQ ID NO:19), GSIKIRGTYS (SEQ ID NO:20), GSINNNR (SEQ ID NO:21), SDPGYIGSR (SEQ ID NO:22), YIGSR (SEQ ID NO:23), GTPGPQGIAGQGVV (SEQ ID NO:24), GTPGPQGIAGQRVV (SEQ ID NO:25), MNYYSNS (SEQ ID NO:26), KKQRFRHRNRKG (SEQ ID NO:27), CRGDGGGGGGGGGGGGPHSRN (SEQ ID NO:28), CPHSRNSGSGSGSGSGRGD (SEQ ID NO:29), Acetylated-GCYGRGDSPG (SEQ ID NO:30), CRDGS (SEQ ID NO:31), cyclic RGD{Fd}C (SEQ ID NO:32), RKRLQVQLSIRT (SEQ ID NO:33), IKVAV (SEQ ID NO:34), YIGSR (SEQ ID NO:35), KRTGQYKL (SEQ ID NO:36), TYRSRKY (SEQ ID NO:37), KRTGQYKLGSKTGPGQK (SEQ ID NO:38), QAKHKQRKRLKSSC (SEQ ID NO:39), SPKHHSQRARKKKNKNC (SEQ ID NO:40), XBBXBX, wherein B=basic residue and X=hydropathic residue (SEQ ID NO:41), XBBBXXBX, wherein B=basic residue and X=hydropathic residue (SEQ ID NO:42), and RGDSP (SEQ ID NO:43).

The present disclosure further may include a spacer peptide between the plant adhesion molecule and cell adhesion peptide. The addition of a spacer in the peptide sequence ensures that the conjugation with the plant adhesion molecule (e.g., dopamine-containing compound) does not affect the bioavailability of the cell adhesion peptide. Suitable spacer peptides for use herein include, for example, poly-glycine or glycine-rich sequences (e.g., GGG, GSGSGS (SEQ ID NO:44), etc.)

To aid in conjugation, cross-linking agents are used. Suitable cross-linking agents include, for example, 1-Ethyl-3-(3-dimethylaminopropyl)-carbodiimide (EDC) and N-hydroxysuccinimide (NHS), aldehydes (e.g., glutaraldehyde), isocyanates, plant extracts, and the like and combinations thereof.

The concentration of conjugated plant adhesion molecule and cell adhesion peptide for coating the decellularized plant tissue will depend on the specific cell adhesion peptide being used and the desired cells to be adhered to the decelluarized plant tissue. Typically, however, the decellularized plant tissue is coated with from about 0.1 mg/mL to about 1 mg/mL conjugated plant adhesion molecule and cell adhesion peptide.

The plant scaffolds of the present disclosure can be used to alter (e.g., enhance, inhibit and change) cell function, and in particular, cellular expansion, maturation and differentiation. It has been advantageously found that cells can expand, mature and differentiate such to provide tissues having improved microvasulature structure, that is, vasculature beyond the 100-200 µm diffusion limit, suitably, above the 200 m diffusion limit.

Cells can be analyzed for cell attachment, cell spreading, cell morphology, cell proliferation, cell migration, cell expansion, cell differentiation, protein expression, cell-to-cell contact formation, sprouting, tubulogenesis, formation of structures, and combinations thereof.

In particularly suitable embodiments, the plant scaffolds can be used to engineer tissue, and in particular, mammalian tissue. Generally, method of engineering mammalian tissue includes culturing a cell within the plant scaffolds prepared in the present disclosure. The methods use the perfusable plant scaffolds to provide tissue having a microvasculature structure.

EXAMPLE 1

In this Example, plant tissues were decellularized and functionalized as described in the present disclosure. The ability of the functionalized, decellularized plant tissue to act as a scaffold for cell expansion was then analyzed.
Methods:
Decellularization of Plant Tissues:

Most of the plants used in this Example (*Calathea Zebrina, Anthurium waroquaenum, Anthurium magnificum, Solenostemon wasabi*, Vanilla, *Laelia ancepts*, Bamboo) were obtained from the Olbrich Botanical Gardens in Madison, Wis. Among the available tropical plants, plants with stems of high porosity and fast growth rate were selected to ensure continuity of supply for the Example and for potential applications. Parsley was purchased from a local market and *Schoenoplectus tabernaemontani* plants were collected at the UW Arboretum. Leaves and stems were collected from fresh plant tissues to minimize disruptions to the tissues structure. Leaves were cut into discs using 8 mm punches, while stems were manually cut at about 8 mm in length. Plant tissues were then immersed in a solution of 10× sodium dodecyl sulfate (SDS) in water for 5 days in gentle agitation. Successively, the tissues were incubated in 0.1% Triton-X-100 in a 10% solution of bleach for 48 hours. After which, the stems and leaves lost all their pigments and turned white. The waxy cuticle was dissolved by 1 minute incubation in hexane followed by 1 minute wash in 1× phosphate buffered saline (PBS), the process was repeated at least twice. Deionized water was used to remove eventual residues of detergents and bleach, the tissues were incubated in H$_2$O for at least 2 days, after which were lyophilized and stored dry until needed.

RGDOPA Synthesis:

A custom peptide with the sequence RGDGGG (SEQ ID NO:45) was purchased from GENSCRIPT®. The peptide was reconstituted at a concentration of 16 mM in a buffer solution of 10 mM 2-(N-morpholino)ethanesulfonic acid (MES) at pH 6. While stirring, dopamine hydrochloride (Sigma-Aldrich, H8502) was also dissolved into this solution at a final concentration of 200 mM. The conjugation of dopamine to the custom peptide was obtained by using the zero-length crosslinking agent 1-Ethyl-3-(3-dimethylaminopropyl)-carbodiimide (EDC) and N-hydroxysuccinimide (NHS). NHS (ThermoFisher Scientific, 24500) was first added to the reaction mix at a concentration of 5 mM and successively EDC (Sigma-Aldrich, E6383) at a concentration of 0.1M. The reaction mix was stirred for 2 hours at room temperature and then dialyzed using a 100-500 Da dialysis membrane (Spectrum Labs, 131060) in deionized water for 5 days. The purity of the reaction product was assessed by High Performance Liquid Chromatography (HPLC). RGDOPA was then lyophilized and stored dry at −20° C.

Plant Tissue Functionalization with RGDOPA:

Plant's stems or leaves were washed in a solution of 10 mM Tris-HCl at a pH of 8.5 and incubated at room temperature for 30 minutes under gentle agitation. In the meantime, RGDOPA powder was reconstituted in 10 mM Tris-HCl (pH 8.5) at a final concentration of 1 mg/mL. Plant tissues to be functionalized were then immersed in the RGDOPA solution and incubated for 24 hours under gentle agitation at room temperature. After functionalization, plant tissues acquired a slightly grey/black color. To remove unbound RGDOPA, the tissues were then washed twice in 10 mM Tris-HCl (pH 8.5) and once in PBS (1×) prior to be used for cell culture.

Mineralization of Plant Stems:

To form a mineralized coating, plant's stems were incubated in modified simulated body fluid (mSBF) for 7 days under gentle agitation. The mSBF was prepared by adding the following reagents into deionized water in the following order: 141 mM NaCl, 4 mM KCl, 0.5 mM MgSO$_4$, 1 mM MgCl$_2$, 150 mM NaHCO$_3$, 20 mM HEPES, 5 mM CaCl$_2$) and 2 mM KH$_2$PO$_4$. The pH of the mSBF was then adjusted to 6.8 and throughout the 7 days of coating, the mSBF solution was changed daily. After the 7 days of coating, plant stems were rinsed in deionized water and lyophilized.

Sample Preparation for Scanning Electron Microscope (SEM) Imaging:

Immediately after collection, the samples were immersed in a buffered solution of 2% paraformaldehyde (PFA) in 1×PBS for maximum 30 minutes. A more extensive fixation was obtained by incubating the samples in 1.5% Glutaraldehyde in freshly prepared 70 mM sodium Cacodylate buffer pH 7.4. The samples were then rinsed in 70 mM Sodium Cacodylate buffer with the addition of 2.5% sucrose and dehydrated by immersion in a graduated series of ethanol in H$_2$O and hexamethyldisilazane (HDMS) in ethanol baths of respectively 30, 50, 80 and 95%. The samples were left to dry on the sample holder and then gold sputter coated prior imaging in SEM.

Quantification of Water Retention:

Lyophilized plant's stems were weighed dry (n=4) and then immersed in 2 mL water for 1 hour at room temperature. Successively, the wet stems were weighed a second time and the weight difference was considered as the amount of water retained by the stems.

Pore Size Quantification:

Normal and decellularized stems were characterized using SEM. Images were analyzed using the software ImageJ and the diameter of at least 50 pores per stem was measured from at least 3 different images.

Cell Imaging:

Calcein staining was used to perform live-cell staining. Samples were incubated for 30 minutes in 10 mM calcein (Life Technologies, C3099) and subsequently washed in PBS 1×. Each sample was imaged using a fluorescence microscope. Cell cytoskeleton instead, was stained using phalloidin. Samples were incubated for 2 hours in rhodamine-phalloidin (Cytoskeleton Inc., PHDR1) according to the supplier's protocol and 10 min in 4',6-diamidino-2-phenylindole (DAPI) to stain the nuclei Images were acquired by using a fluorescence microscope.

Quantification of Cellular Orientation:

To quantify cellular orientation, it was assumed that nuclear shape is related to cell shape as the link between these two features has been highlighted in a number of studies. Nuclear shape was assessed by analyzing images of DAPI-stained cells using the software cellProfiler. The captured images were rotated following the direction of the topographical features of the stems (monolayer controls were rotated randomly). The background of the images was subtracted and the threshold was set manually for each individual image to avoid the quantification of artifacts. Also, each object was filtered using size criteria, only objects with a size comprised between 1 and 50 µm were counted. The software then measured the angle between the longest side of the cell's nuclei and the topographical features of the stems. Only cells oriented within a specific degree range (20°, 30° and 40°) were counted and normalized over the total number of cells.

Quantification of Cellular Metabolic Activity:

Cellular metabolic activity was assessed using the CELL-TITER-BLUE® assay (Promega, G8081) and following the manufacture's protocol. Briefly, a 24-well plate was used to culture cell-laden stems, 40 µL of CELLTITERBLUE® were added in each well and incubated at 37° C. for 24 hours. The following day, 100 µL were collected from each sample and transferred to a black 96-well plate. The fluorescence signal was recorded ($560_{ex}/590_{em}$) using a multi-plate reader. Even though stems were cut to the same length, they had different diameters, thereby having different seeding surfaces. Cells had the tendency to grow on the outer part of the stems, for this reason, it was decided to consider only the external surface of the stems as "seeding area". The seeding area was calculated using the formula: $A=2\pi rh+2\pi r^2$ because of the cylindrical shape of the stems.

Histological Analysis:

Stems were cut into approximately 1 cm length pieces. Samples were fixed overnight in an ATP-1 automatic tissue processor (Triangle Biomedical Sciences, North Carolina) prior to being paraffin embedded. Embedded tissues were sectioned in 14 µm slices. Sections were stained using Sass's Safranin-O and Fast Green. In short, sections were stained for 1 hour in aqueous 1% (w/v) Safranin-O and then rinsed in deionized water for 5 minutes. Tissues were then dehydrated serially in 70% and then 95% ethanol for 3 minutes each. Sections were then dipped for 10 seconds in Fast Green FCF (0.1% w/v in 95% ethanol). After dipping, sections were washed of excess stain in two changes of 100% ethanol for 2 minutes per change and then cleared in two changes of xylene for 2 minutes per change. Samples were then mounted with a coverslip and sealed with Cytoseal XYL (Thermo Fisher Scientific, Waltham, Mass.) Images of tissue sections were visualized using a DMLB2 upright microscope (Leica Microsystems, Buffalo Grove, Ill.). Further stains performed on cell-laden stems were H&E and Masson's Trichrome.

DNA Quantification:

Native and decellularized parsley stems were cut into 1 cm long sections and placed into microcentrifuge tubes. Tissues were snap-frozen by being dropped into liquid nitrogen for 1 minute. Frozen tissue pieces were ground with a mortar and pestle and then further processed by being pulled through a 22-gauge syringe needle. Samples were further broken up through sonication. DNA was quantified from pulverized samples using a CyQUANT Direct Cell Proliferation Assay (Thermo Fisher, Waltham, Mass.). Concentrations were determined using a Victor3 spectrophotometer (Perkin Elmer, Waltham, Mass.).

NMR Analysis of Conjugated Peptide:

The conjugation of dopamine to RGD peptide was verified with 1H nuclear magnetic resonance (NMR) spectroscopy. 1H NMR spectra were recorded using Bruker Avance III (500 MHz) in $D_2O$ supplemented with 4,4-dimethyl-4-silapentane-1-sulfonic acid (DSS) as an internal standard.

Mechanical Testing:

Normal and mineralized parsley stems were cut into 2 mm long sections. The ends of the stem sections were sealed with silicon glue between two pieces of vellum paper in order to ensure a strong grip and uniform strain. Stems were uniaxially stretched at a constant rate of 5 mm/min in an Electro-Puls E1000 tester (Instron Corp., Norwood, Mass.). Maximum tangent modulus, ultimate tensile strength, and strain at failure were calculated. Maximum tangent modulus was established by fitting a line to the maximal sloped linear region of the stress-strain graph. Ultimate tensile strength and strain at failure were calculated from the generated stress-strain graphs.

Figure 3M:
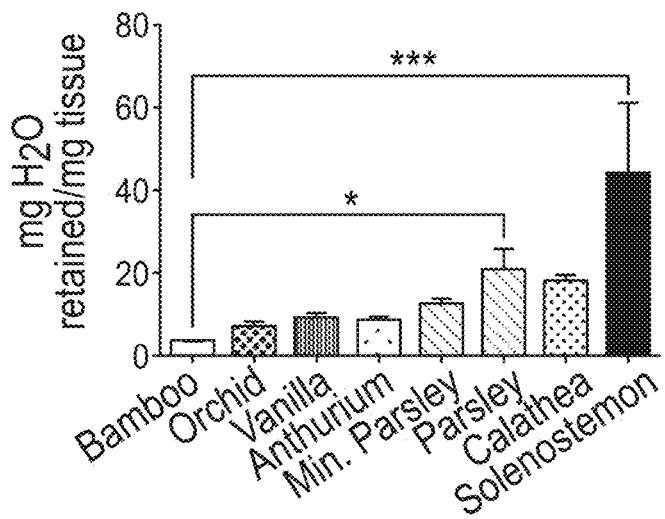
FIG. 3M depicts the mass of water retained normalized to each stem's mass. (*) represents statistically significant differences using one-way ANOVA followed by Tukey's multiple comparisons test, n=4, $*p<0.05$ and $***p<0.001$.
Figure 3N:
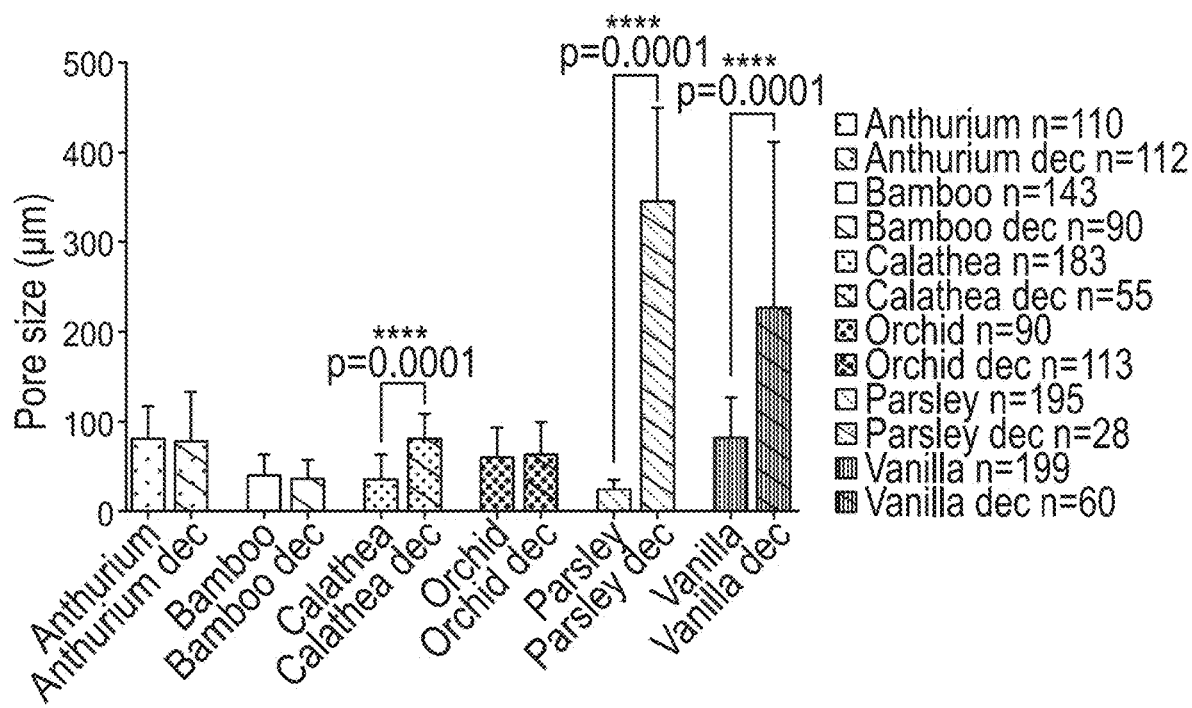

Results and Discussion:

As illustrated in FIG. 1A, portions of desired sizes were cut from fresh plants and decellularized. PICOGREEN® assay revealed that decellularized parsley stems showed a more translucent appearance due to the loss of the plant's pigments and waxy cuticle, and also had a markedly decrease in DNA content when comparted to non-decellularized parsley stems (FIGS. 1B & 1C & FIGS. 2A & 2B). Electron micrographs of plants before and after decellularization (FIGS. 3A-3N) showed a highly porous ultrastructure, with pore sizes below 100 μm (FIG. 3N). As expected, stems from monocot plants such as *Vanilla planifolia* (Vanilla) had vascular bundles scattered throughout their cross-section (FIG. 3K), while dicot plants like parsley (FIG. 3I; FIGS. 4A-4E) had their vascular bundles arranged in a ring surrounding the pit. Stems maintained their porosity after decellularization (FIGS. 3A-3I), and the ultrastructure was unchanged in the *Laelia ancepts* (orchid) pseudobulbs, *Anthurium waroqueanum* (Anthurium) and *Bambusoideae* (bamboo) stems (FIG. 3N). However, the size of pores was significantly enlarged in *Calathea zebrina* (Calathea), parsley and vanilla stems, with parsley stems showing the largest increase in pore size (FIG. 3N). Decellularized stems were also able to retain substantial amounts of water, consistent with the mechanism for hydraulic continuity in plants. Stiffer stems like bamboo were able to retain almost 4 times their weight in water, while softer stems from parsley and *Solenostemon scutellarioides* 'wasabi' (Solenostemon) were able to retain more substantial amounts of water (20 and 40 times respectively, FIG. 3M). The ability of decellularized plants to retain their hierarchical, hydrophilic, and interconnected ultrastructure led us to explore the ability of plants to serve as scaffolding for mammalian cells.

Figure 5A:
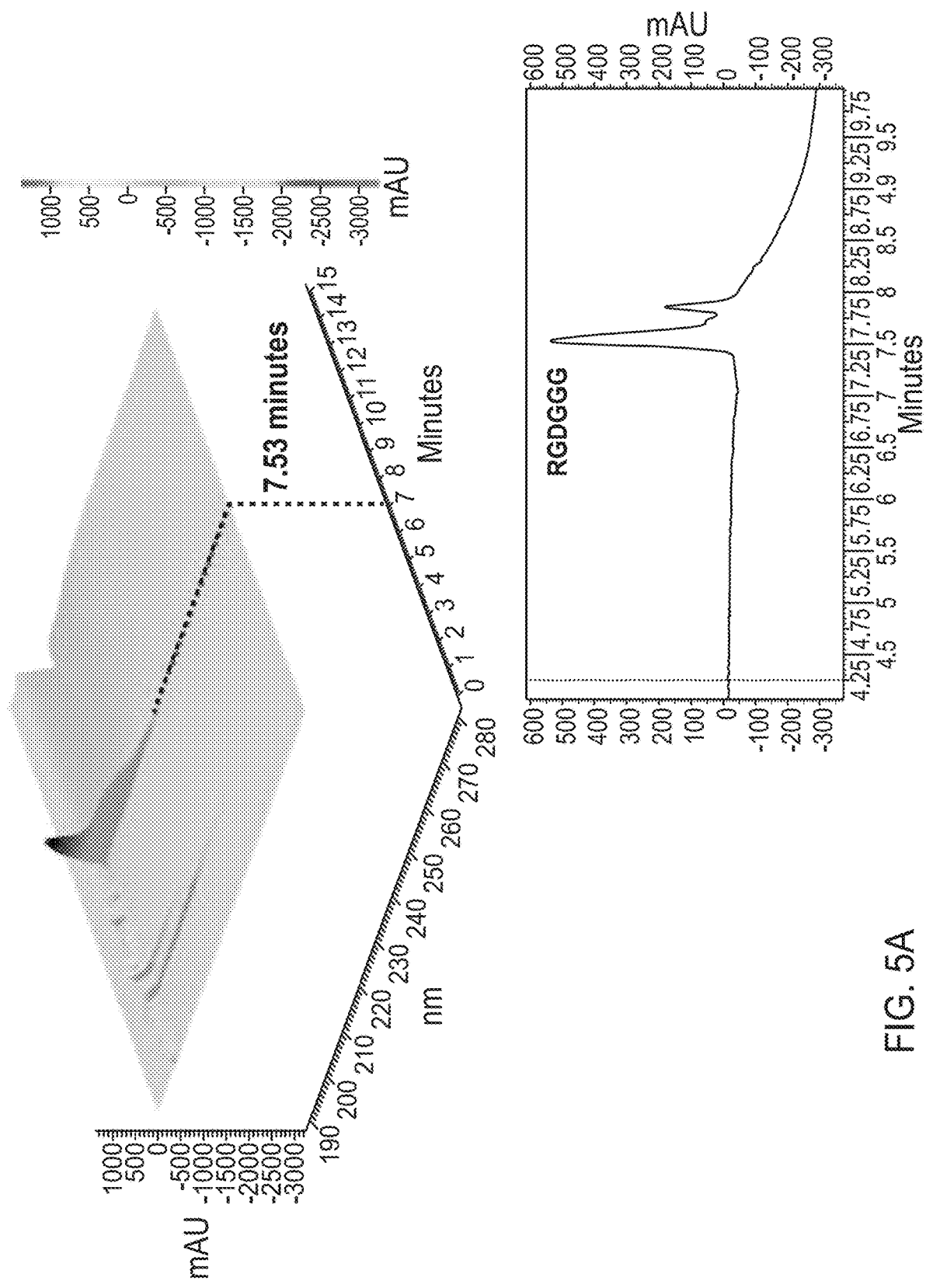
FIGS. 5A & 5B depict high purity of RGDOPA after dialysis.
Figure 5B:
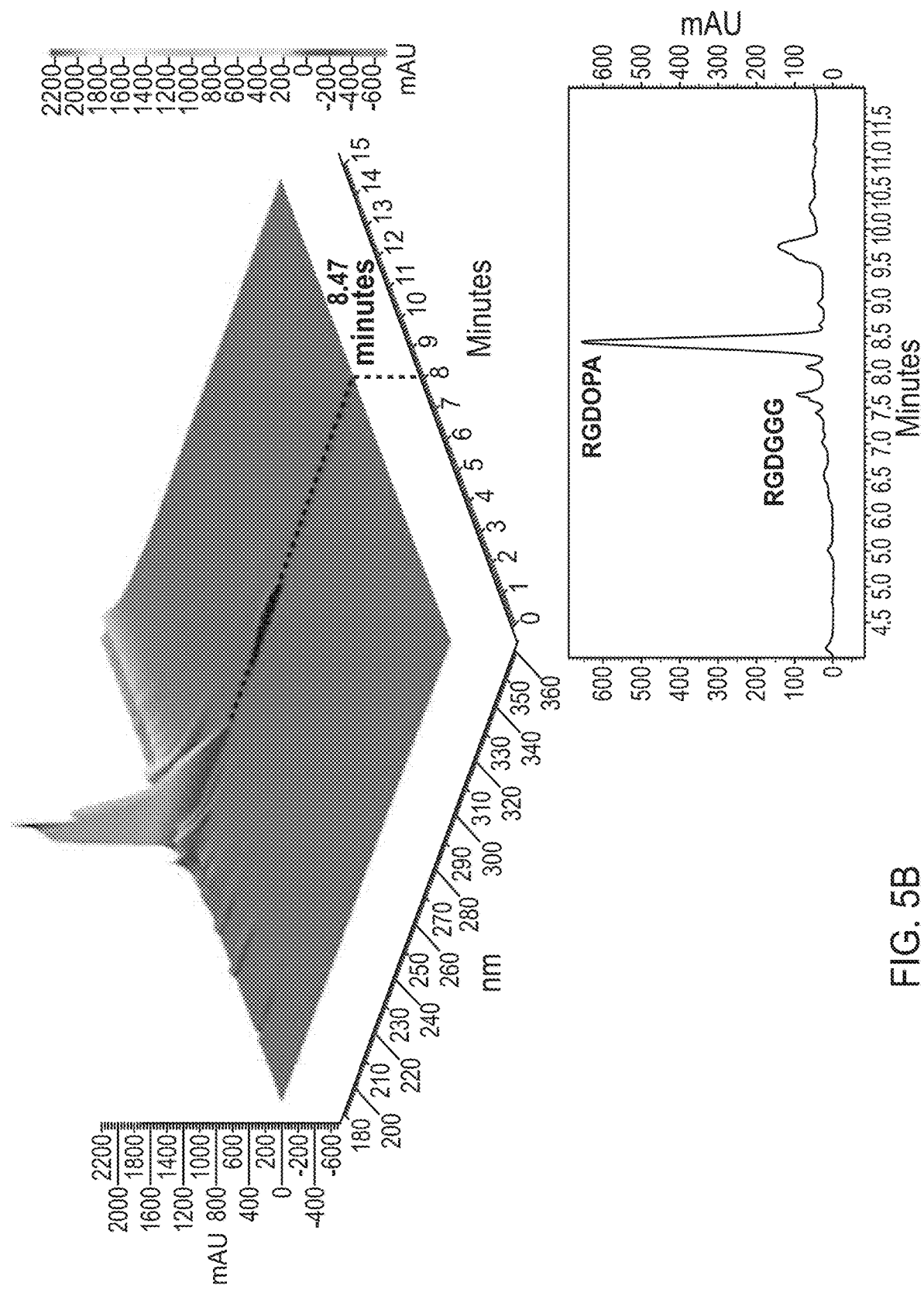
Figure 5C:
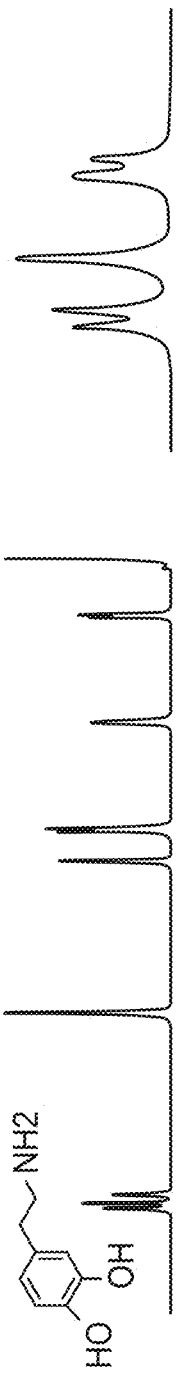
FIGS. 5C-5E depict NMR confirms the presence of dopamine in RGDOPA: 1H NMR spectra of (FIG. 5C) dopamine, (FIG. 5D) RGDGGG and (FIG. 5E) RGDOPA. Shown in right column are the enlarged spectra in the range of 6.5 to 7.1 ppm to monitor the presence of aromatic protons.
Figure 5D:
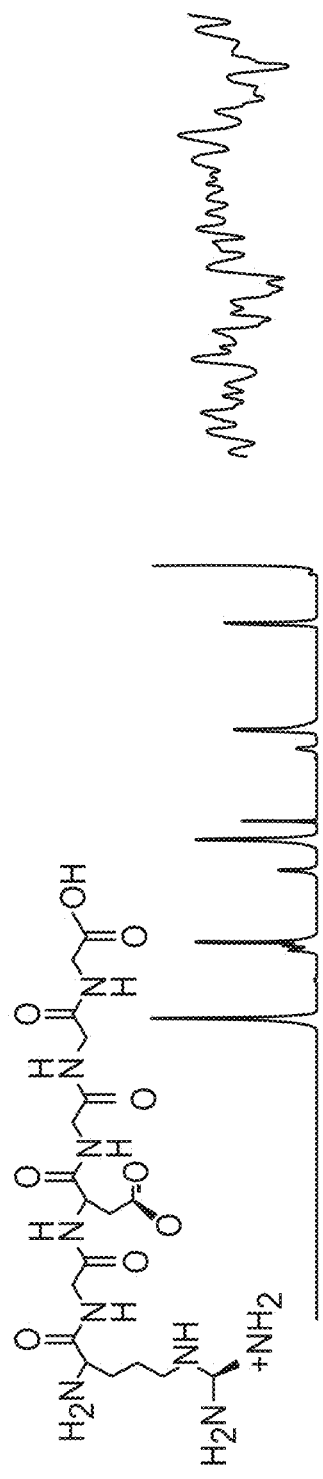
Figure 5E:
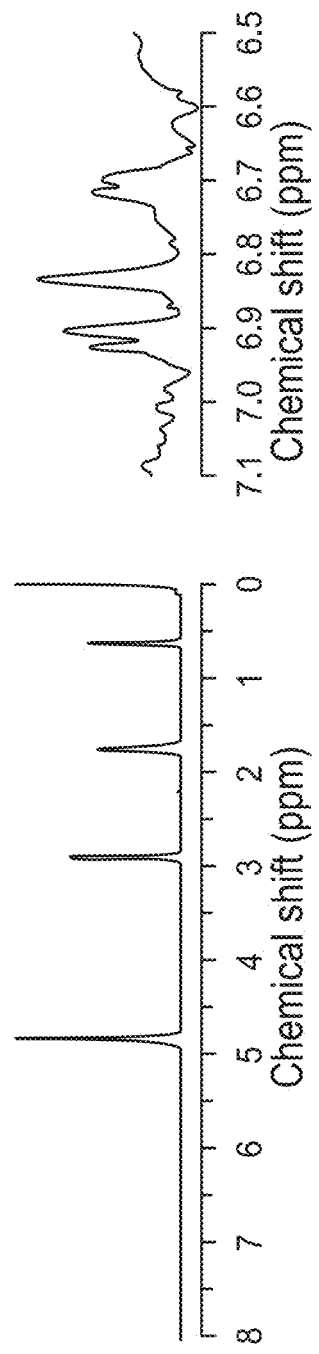
Figure 5F:
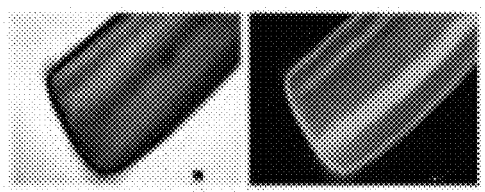
FIGS. 5F-5N depict effective RGDOPA functionalization of plant stems: To assess if DOPA-conjugated RGD peptides (RGDOPA) are effective in functionalizing plant stems a FITC-labelled RGD peptide was used and its binding kinetics to the stems was monitored for a period of 16 hours.
Figure 5G:
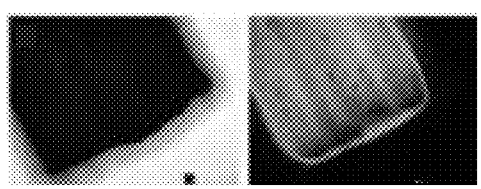
Figure 5H:
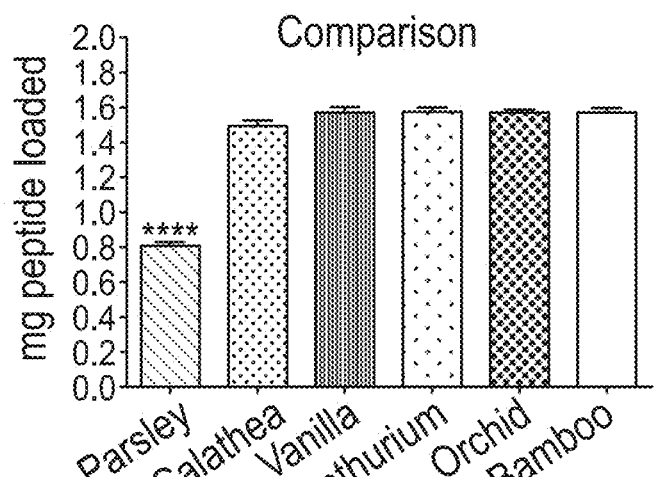
Figure 5I:
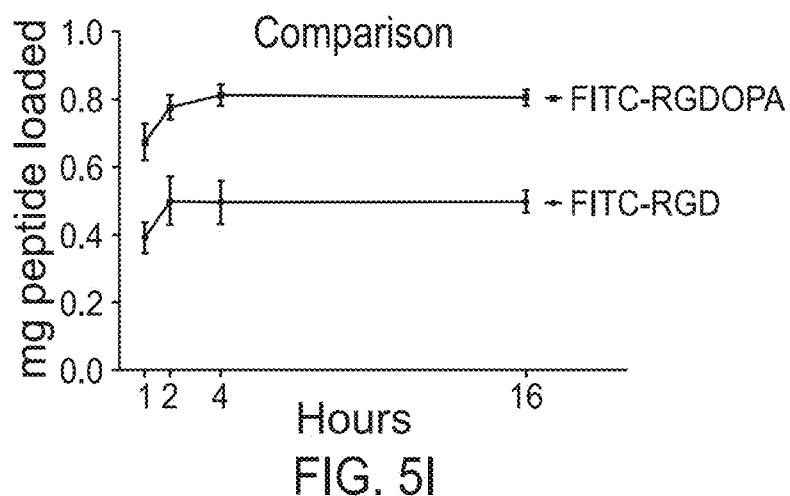
Figure 5J:
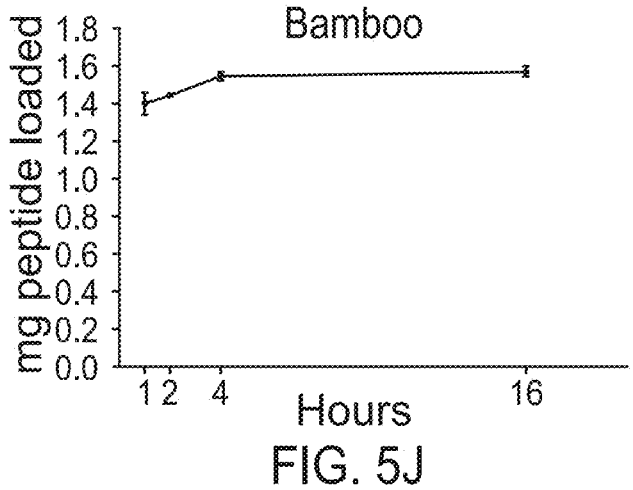
Figure 5K:
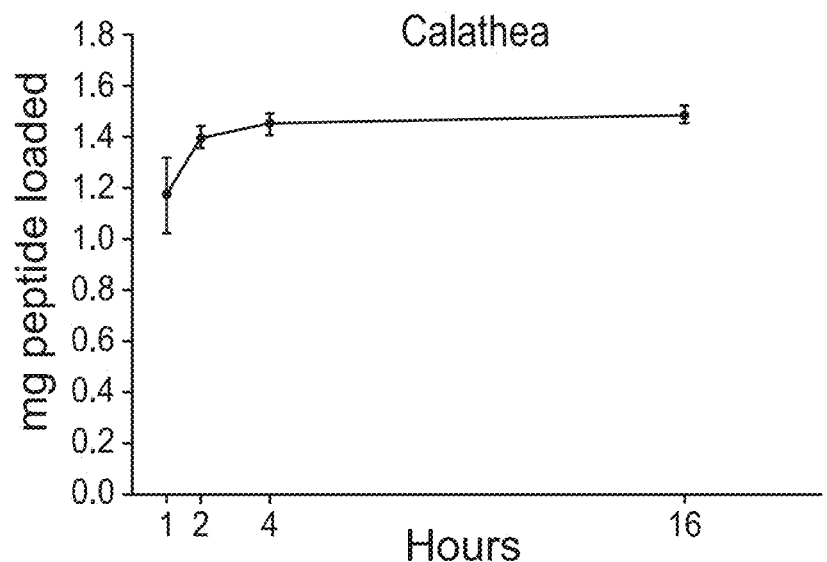
Figure 5L:
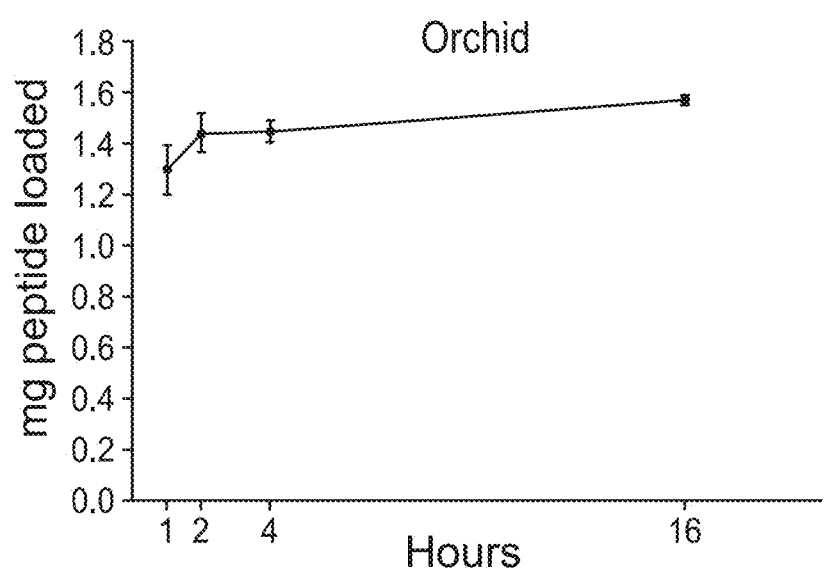
Figure 5M:
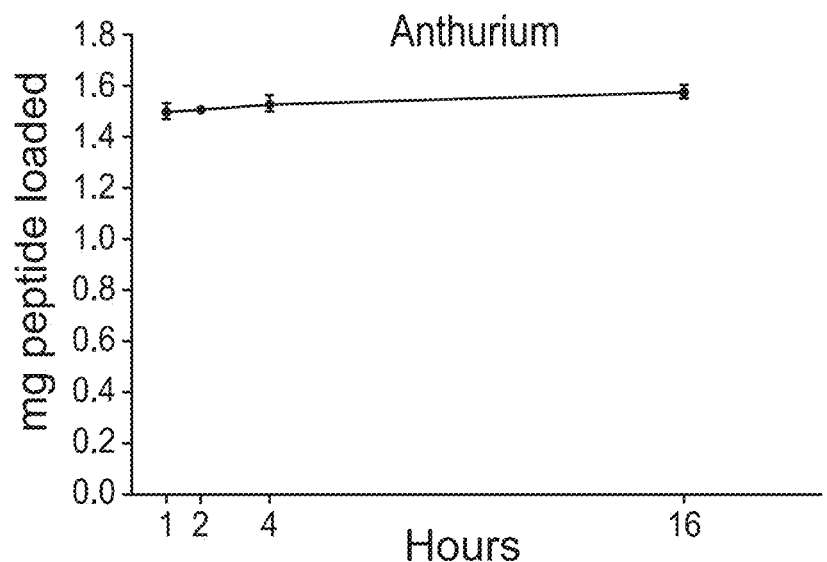
Figure 5N:
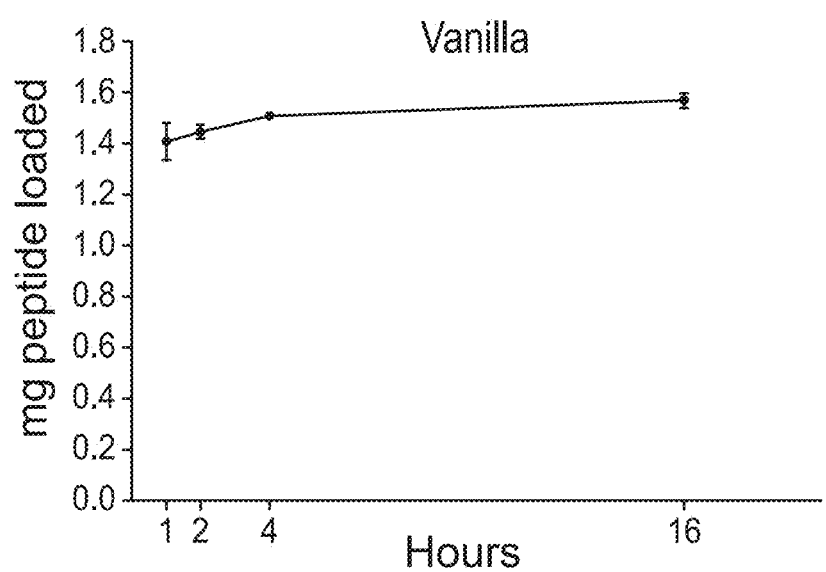
Figure 7A:
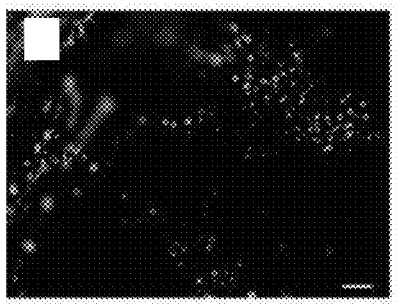
FIGS. 7A-7F depict hDF seeded on RGDOPA-coated *Impatiens capensis* stems.
Figure 7B:
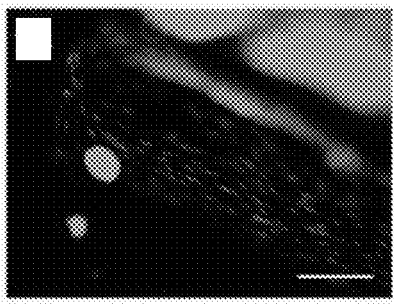
Figure 7C:
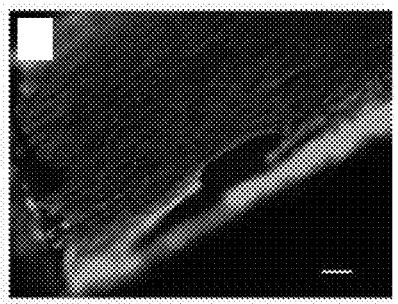
Figure 7D:
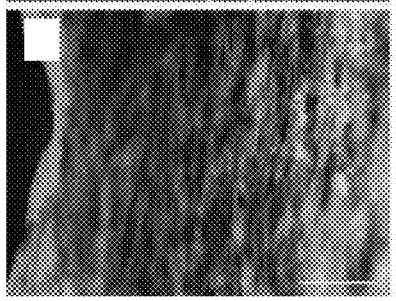
Figure 7E:
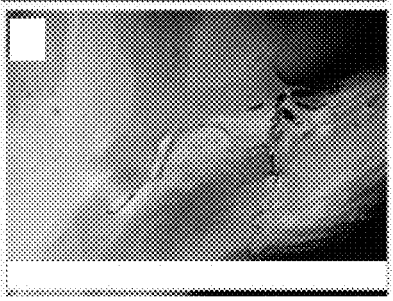
Figure 7F:
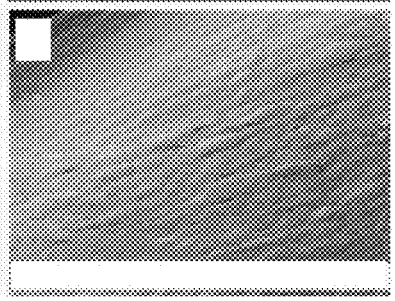
Figure 8C:
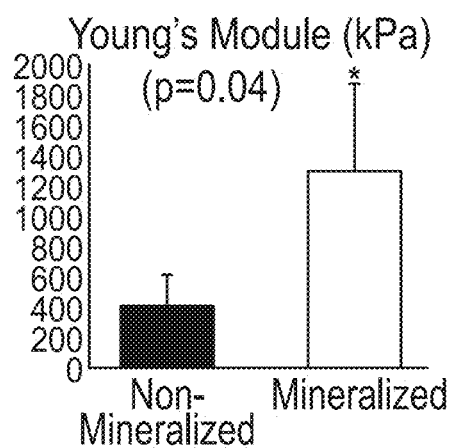
Figure 8D:
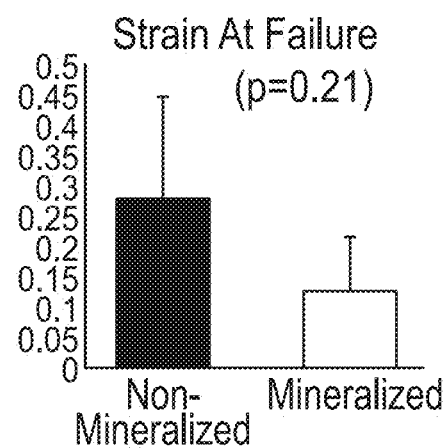
Figure 8E:
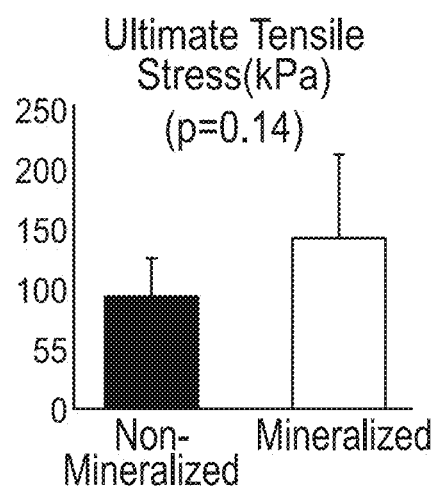
Figures 10A, 10B, 10C, 10D, 10E, 10F:
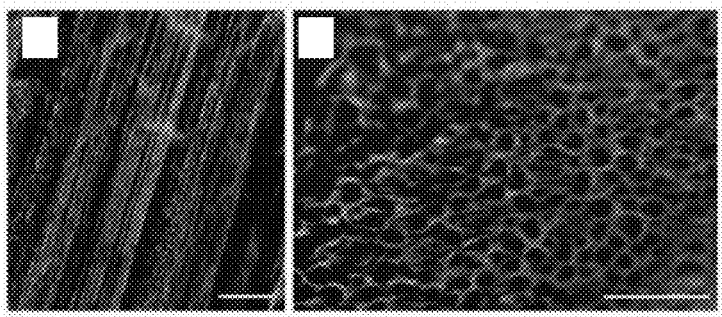

To provide a mechanism for cell attachment on a heterogeneous set of plant surfaces, RGD peptides were conjugated with dopamine (FIGS. 5A-5N). Decellularized plants coated with the RGD-dopamine conjugate (RGDOPA) supported adhesion of human dermal fibroblasts (hDF), while non-coated plants did not support cell attachment on parsley stems (FIGS. 6A-6I) and *Impatiens capensis* stems (FIGS. 7A-7F). A further advantage of the RGDOPA coating was its ability to functionalize plant tissues without clogging pores, thereby maintaining their topographical features and only minimally affecting their surface area (FIGS. 6H & 6I and Table 1). Decellularized plants were also functionalized via biomineralization (FIGS. 8A-8E), a method used in a variety of previous studies to coat biomaterials. Biomineralized plants also supported attachment of hDF (FIG. 6B). Scanning electron microscopy (SEM) showed that the biomineralization process preserved the structural features of vascular bundles and larger pores in dicot stems (FIG. 6G), but also changed the topography of decellularized stems (FIG. 6F, FIGS. 9A-9F) and occluded some of the smallest pores (Table 2).

TABLE 2

BET analysis of decellularized stems

| Sample | Total Surface Area ($m^2/g$) | Average pore Diameter (nm) | Total Pore volume (cc/g) |
|---|---|---|---|
| Parsley (non-coated) | 1869 | 4.24 | 1.981 |
| Parsley (RGDOPA) | 1768 | 4.18 | 1.85 |
| Parsley (mineralized) | 523.5 | 4.22 | 0.522 |
| Bamboo (non-coated) | 46.32 | 3.93 | 0.0455 |
| Bamboo (RGDOPA) | 40.41 | 3.97 | 0.0401 |
| Vanilla (RGDOPA) | 193.9 | 3.82 | 0.185 |
| Calathea (RGDOPA) | 142.4 | 3.92 | 0.14 |
| Orchid (RGDOPA) | 212.5 | 4.76 | 0.253 |
| Anthurium (RGDOPA) | 43.34 | 4.53 | 0.049 |

Additionally, as shown in the BET analysis, by using the methods of the present disclosure, a small mass of plant tissues can yield scaffolds with extremely high surface area, which may allow the expansion of high numbers of cells in small volumes.

Figure 11A:
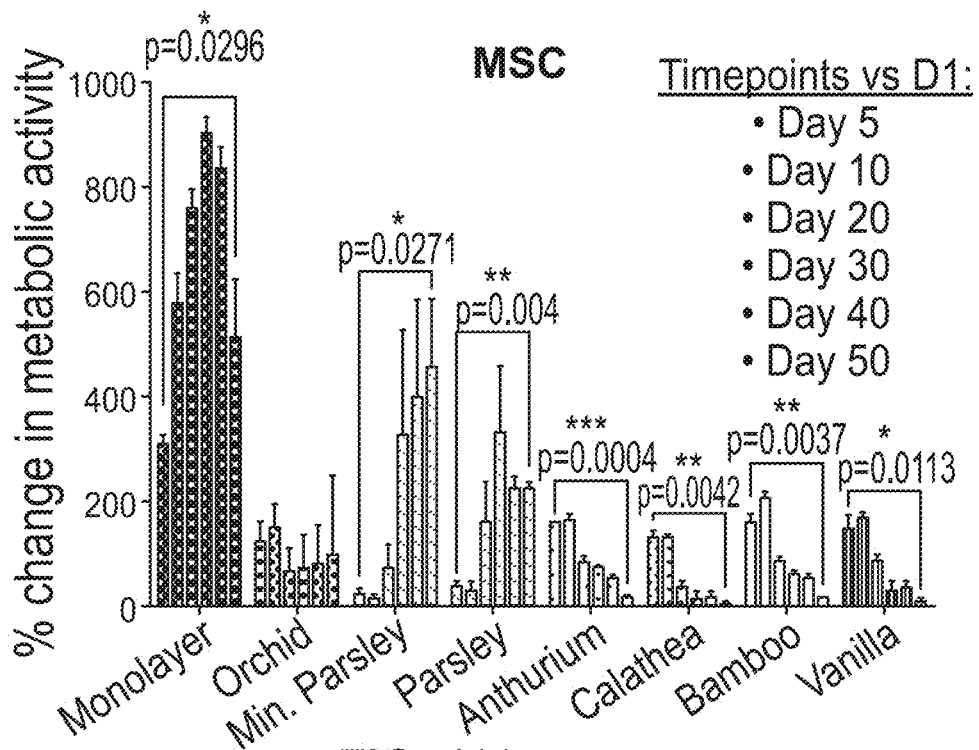
Figure 11B:
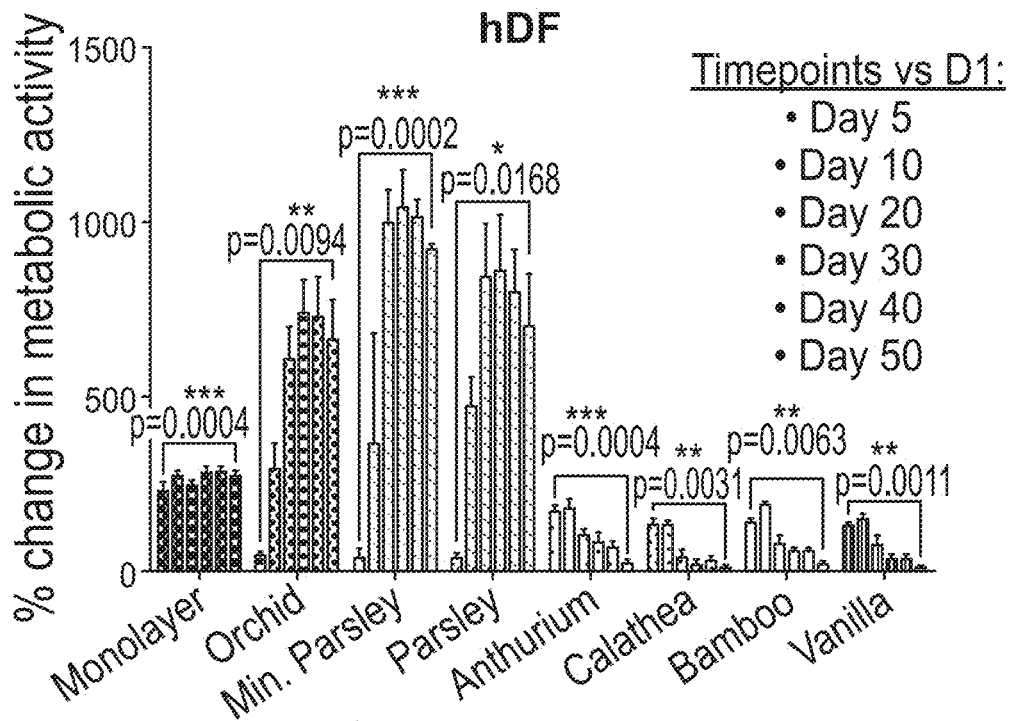
Figure 11C:
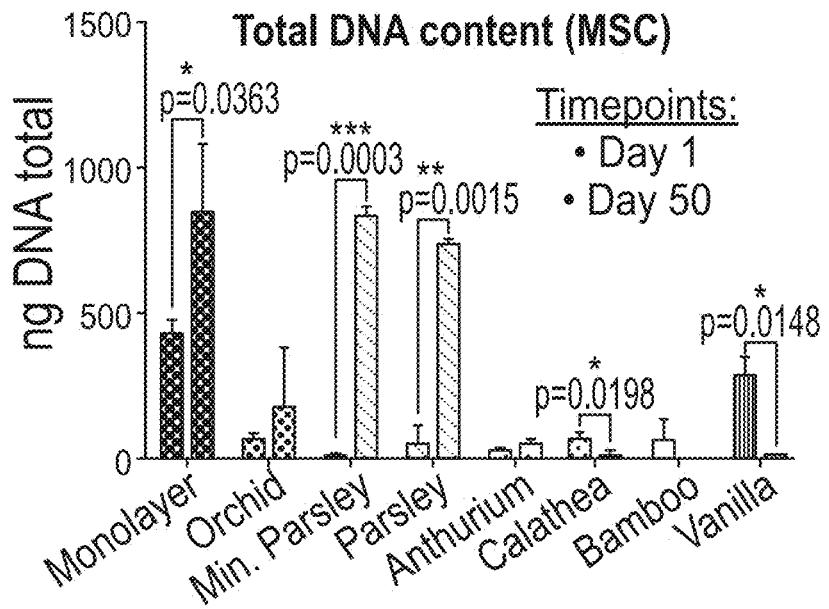
Figure 11D:
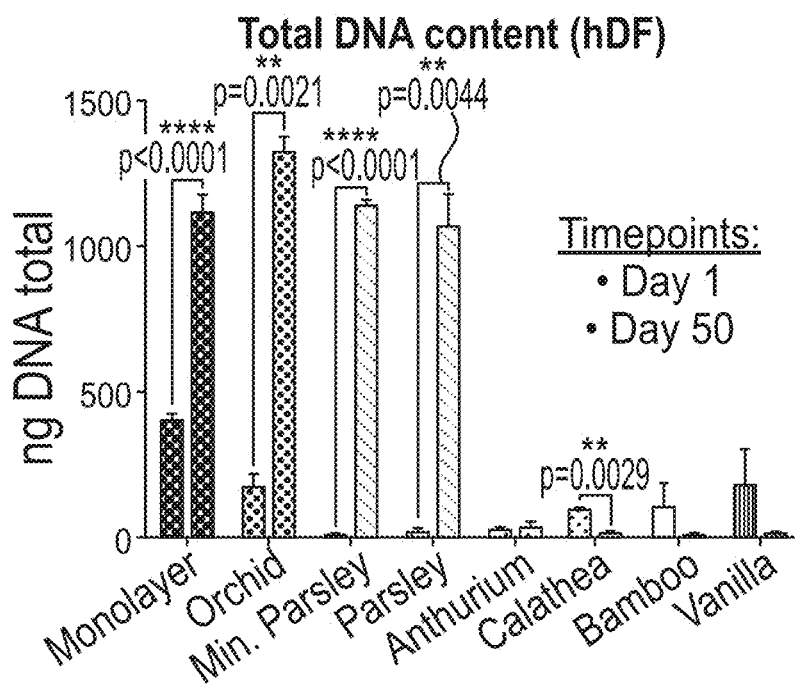
Figure 11E:
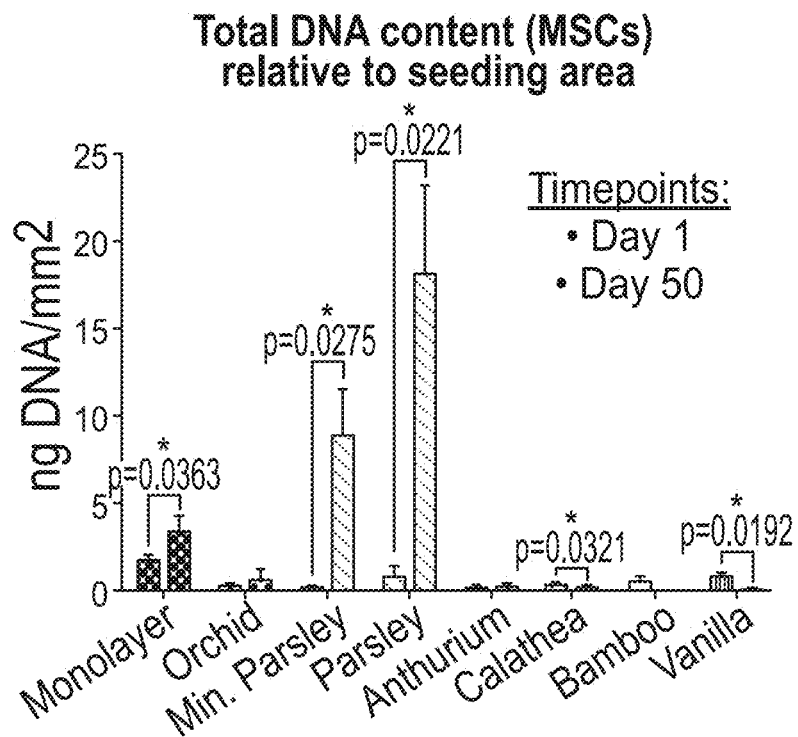
Figure 11F:
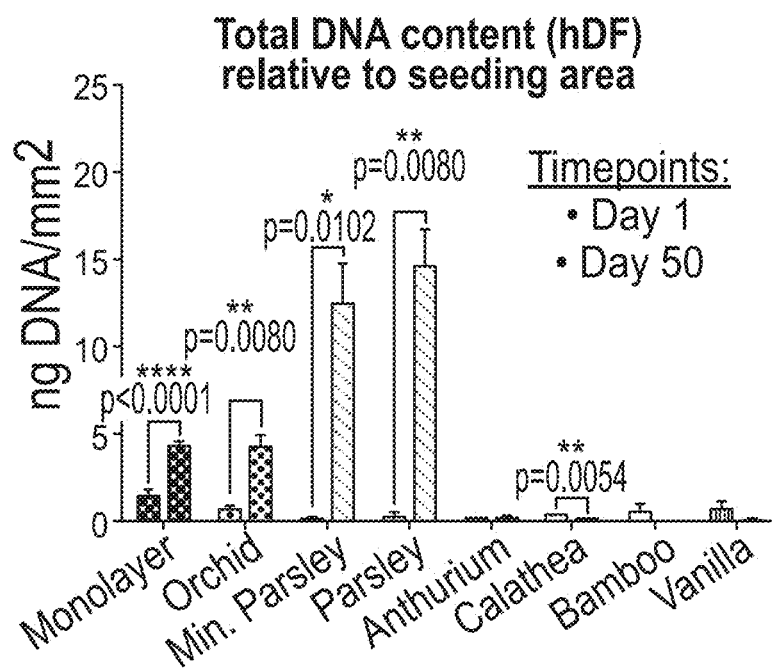
Figure 13A:
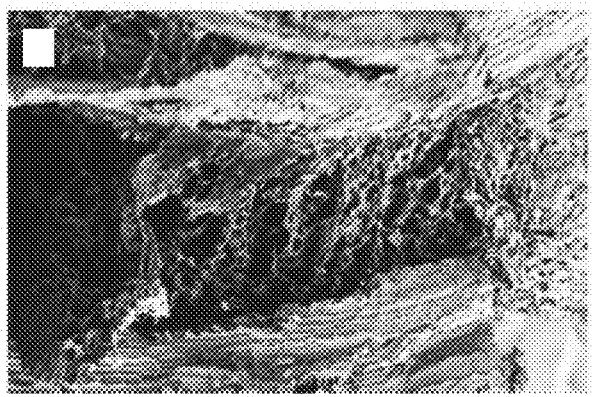
FIGS. 13A-13D depict that hDF can adhere on biofunctionalized plant tissues.
Figure 13B:
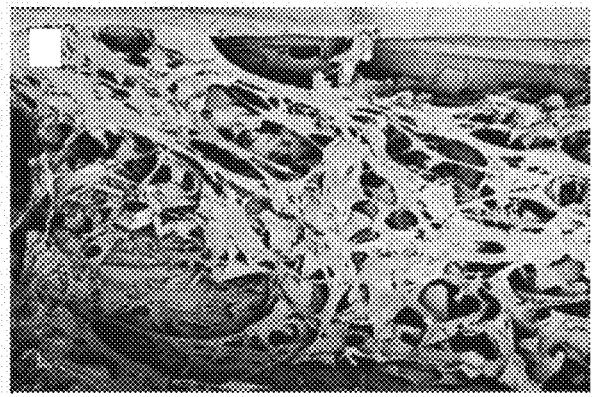
Figure 13C:
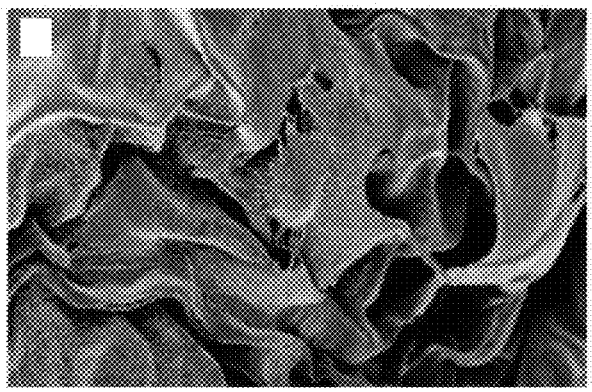
Figure 13D:
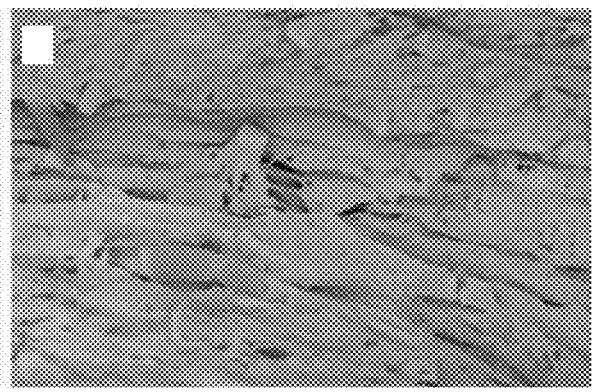
Figure 15A:
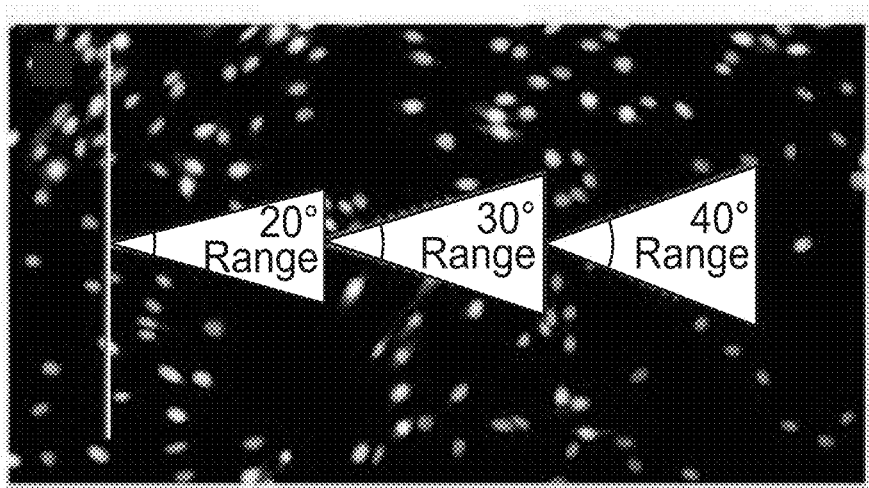
FIGS. 15A-15G show that hDF orientation was influenced by the topographical cues of plant tissues.
Figure 15B:
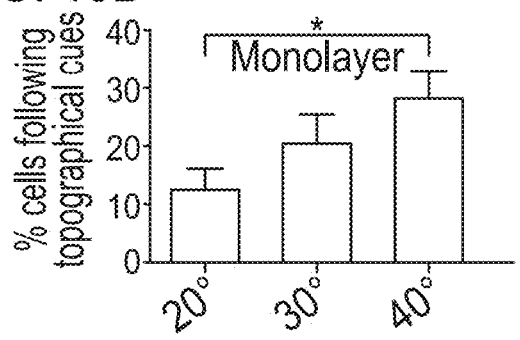
Figure 15C:
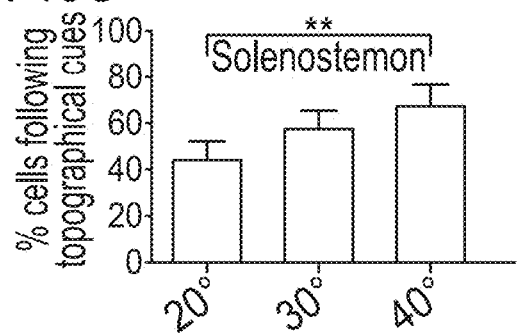
Figure 15D:
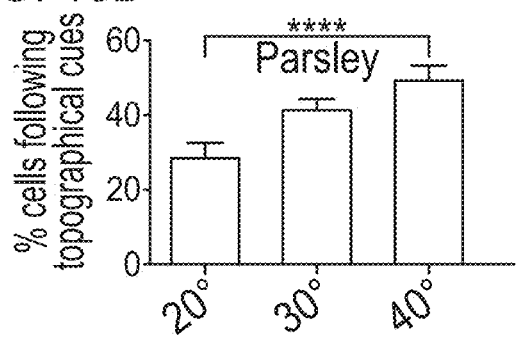
Figure 15E:
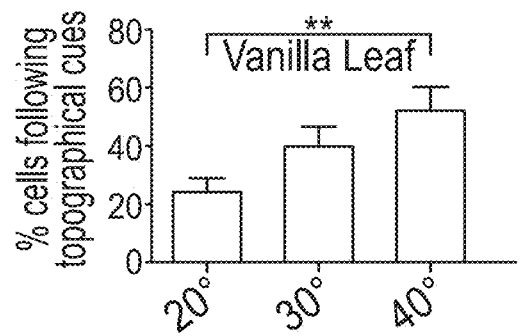
Figure 15F:
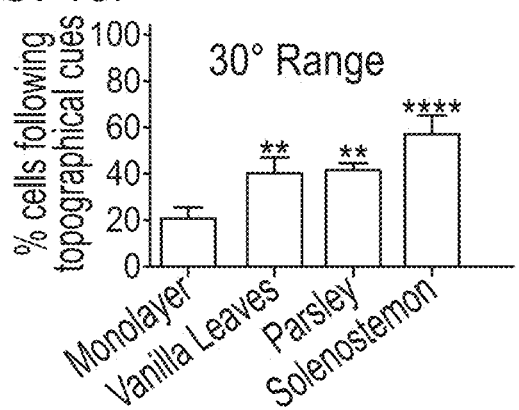
Figure 15G:
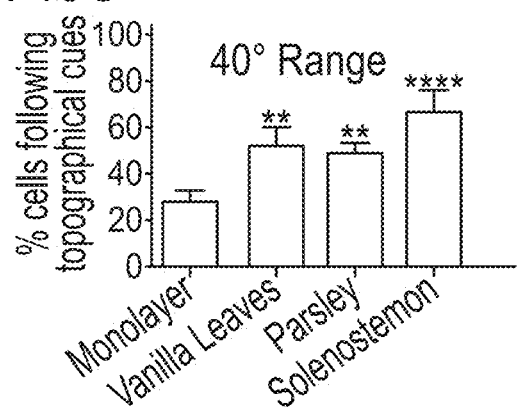
Figure 16A:
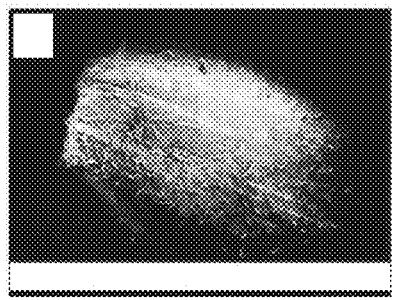
FIGS. 16A-16E show that cells behave differently in different regions of solenostemon stems.
Figure 16B:
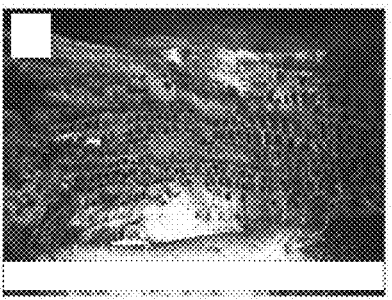
Figure 16C:
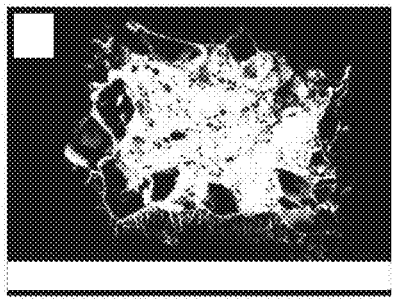
Figure 16D:
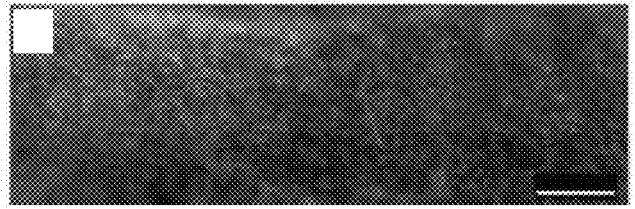
Figure 16E:
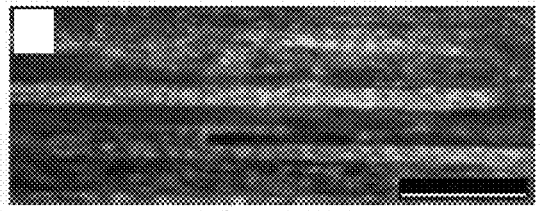
Figure 17:
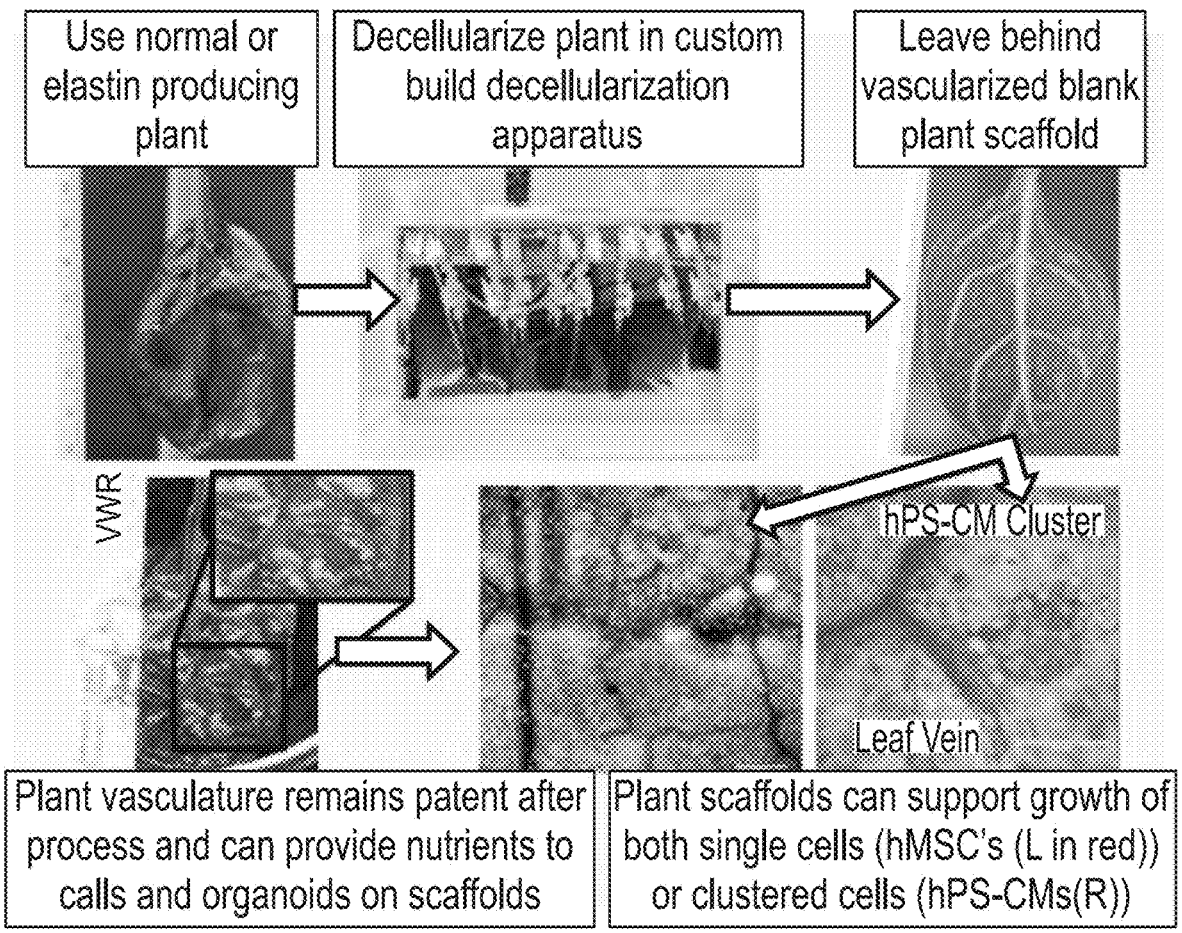
FIG. 17 is a schematic of a method for preparing a decellularized plant tissue scaffold of one embodiment of the present disclosure.
Figure 18A:
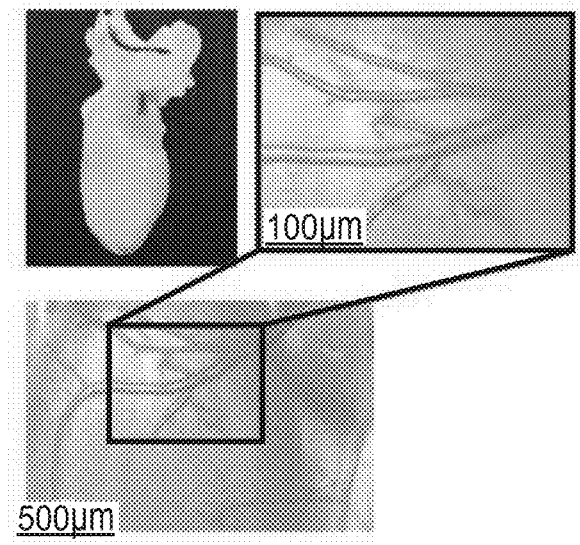
FIGS. 18A & 18B depicts a comparison of mammalian tissue structure and plant tissue structure.
Figure 18B:
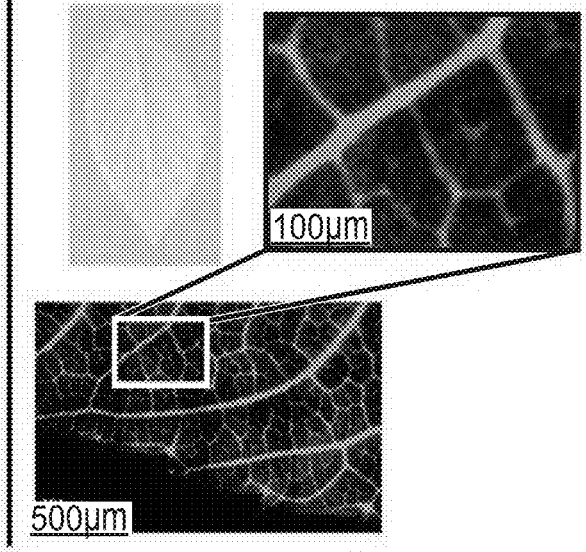

Biofunctionalized plant tissues provided highly efficient and scalable scaffolds for expansion of primary human cells. Human mesenchymal stem cells (MSCs) and human dermal fibroblasts (hDFs) attached to a variety of RGDOPA-coated stems and biomineralized parsley stems, and the cell populations expanded for a period of 50 days. Cells were viable in all stems (FIGS. 10A-10F) and during the first 10 days of culture both cell types showed an increase in metabolic activity in all samples (FIGS. 11A-11L). Over the longer timeframes, the increase in metabolic activity of MSCs was observed only on parsley, mineralized parsley and in standard monolayer culture. This result was confirmed also by DNA quantification, which showed significant MSC expansion in parsley stems, but a significant decrease in cell number in calathea and vanilla stems (FIG. 11C). hDFs seeded on parsley and mineralized parsley showed the highest increases in metabolic activity, and hDFs also expanded significantly on orchid pseudobulbs (FIG. 11D). Importantly, cell expansion efficiency—the cell expansion normalized to the cell seeding area—was substantially higher on plant stems when compared to standard monolayer cultures (Table 2; FIGS. 11A-11L). Specifically, hDFs underwent a 12.5-fold expansion on mineralized parsley stems and a 14.5-fold expansion on RGDOPA-coated parsley stems, versus only a 2.8-fold expansion in standard monolayer culture. Similarly, MSCs expanded 8.7-fold and 17.5-fold on mineralized and RGDOPA-coated parsley stems, respectively, versus only 1.6-fold in monolayer culture. These data indicate that expansion of human cells on the plant scaffolds was highly efficient relative to standard monolayer culture, likely due to the highly interconnected, porous surface area presented by the decellularized plants. Interestingly, the decellularization of plant tissues is a simple process that can yield large scaffolds. For example, the tropical plant *Anthurium magnificum* (length=40 cm, width=30 cm) was used to produce several scaffolds (FIG. 11I), which could each be functionalized with RGDOPA to support adhesion of primary human cells (human umbilical vein endothelial cells, FIGS. 11J-11L).

TABLE 2

Seeding area of decellularized stems

| Sample | Seeding Area (mm$^2$) |
| --- | --- |
| Monolayer Control | 254.34 |
| Anthurium waroqueanum | 293.41 ± 34.52 |
| Vanilla | 318.05 ± 28.09 |
| Solenostemon | 119.77 ± 9.09 |
| Orchid's Pseudobulb | 314.27 ± 47.29 |
| Parsley | 73.22 ± 12.39 |
| Mineralized Parsley | 91.75 ± 17.47 |
| Calathea zebrina | 172.66 ± 31.43 |

The differences in cell expansion among the plants analyzed in this Example may be attributable to differences in plant stiffness, hydrophilicity, pore sizes and overall size. Parsley stems were among the stems with the highest level of hydrophilicity and the largest pore sizes after decellularization (FIGS. 3M & 3N), which may have enabled more efficient cell attachment and expansion. Interestingly, orchid pseudobulbs did not display high hydrophilicity or large pores, yet they supported considerable hDF expansion.

Importantly, human cells conformed to the microstructure of the plant frameworks, resulting in cell alignment and registration between the cell patterns and the plant microstructures. Each leaf or stem used in this Example had unique topographies as a result of the patterning of microgrooves on its surface, and hDFs responded to plant topographical cues by aligning with the characteristic structural patterns of plants (FIGS. 12A-12O and FIGS. 13A-13D). For example, hDFs adhered and grew preferably in proximity to the plant's stomata or within grooves (FIGS. 12A-12O and 14A-14L). To better understand the level of cell alignment to these plant topographies, an "orientation angle" (OA), defined as the angle between the orientation of the plant topography and the orientation of the attached cells (OA=0° would be perfect alignment), was measured. The greatest alignment to the plant's topography was observed on Solenostemon stems (FIG. 12B, FIGS. 15A-15G and FIGS. 16A-16E), where 44.09±7.16% of the cells had an OA less than 20°. In contrast, 28.64±3.39% of the cells on parsley stems had an OA less than 20°. Further, hDFs seeded onto the *Buddleja davidii* (summer lilac) leaf were able to populate the entire leaf and grow around the patterned vascular structure (FIGS. 12N-12O). The cell patterning and alignment observed here on plant scaffolds could be important in future studies, as topographical cues have been used in other contexts to direct cell differentiation, and spatial patterning can facilitate development of complex mammalian tissues.

Another aspect that deserves some consideration is the biocompatibility of the plant tissues. With thousands of different plant species, it is difficult to make general assertions regarding biocompatibility. Some plant species will be more suitable than others for regenerative medicine applications. Particular attention should be devoted in avoiding the use of plants that secrete toxic compounds. In addition, it was found that plants can accumulate heavy metals and other trace elements (TE) from their growth environment with different rates. TE accumulation varies in different categories of plants, for example, it was found to be low in legumes, moderate in root vegetables, and high in leafy vegetables. However, it was further found that TE concentrations in plants are highly related to the chemical composition of the growth media. Therefore, the TE accumulation in plants can be prevented simply by growing plants in controlled environments devoid of heavy metals and other elements that can cause complications. Moreover, eventual TE will most likely be removed by the numerous washes that plant-derived scaffolds undergo during the decellularization process. In fact, the concentration of TE in the decellularized stems was so low that it was not detected at all during the EDS analysis (FIGS. 8A-8E). To date there is only limited knowledge about the tolerance of mammalian tissues to plant tissues in vivo, however, a recent study revealed that subcutaneous implantation of plant-derived cellulose materials evoked only a mild immune response that disappeared 8 weeks post-implantation. This is in line with what has been found following implantation of other cellulosic biomaterials. Interestingly, it was shown that the highly crystalline celluloses evoked no immulogical response. Considering that the degree of crystallinity in many plants is estimated to be around 50%, it can be speculated that limited immunological reactions may be expected after implantation of decellularized plants.

Another issue that should be considered is scaffold degradation. In nature, cellulose (especially in the amorphous form) can be degraded by a family of hydrolytic enzymes called cellulases. However, the tightly packed and orderly structure of crystalline chains of cellulose is impervious to enzymatic degradation. For this reason, cellulosic materials are durable and show limited degradation over time. The recalcitrance of plant tissues could also limit their adoption as scaffolds for regenerative medicine. However, the increase of cellulose-based biomaterials is pushing towards designing novel strategies for controlled degradation in vivo. Some studies have already shown that following hydrolysis pre-treatment and co-delivery of cellulases it is possible to obtain cellulose scaffolds that are resorbable to differing degrees.

Moreover, a new set of enzymes classified as CBM33 and GH61 were recently found to catalyze the oxidative cleavage of polysaccharides. These enzymes are abundant in genomes of biomass-converting microorganisms and are capable of binding effectively to crystalline chains of cellulose and disrupting their structure, thus increasing their accessibility for hydrolytic enzymes such as cellulases. Therefore, degradation of plant-derived scaffolds could be achieved by designing hydrolysis pre-treatments and by the administration of cocktails of cellulases and CBM33 or GH61 enzymes.

As tissue engineering approaches more sophisticated designs, some of the current limitations become more noticeable. For example, design of smaller scaffolds is not always achievable with the literal downsizing of conventional engineering techniques. The resulting scaffolds have limited resolution, high costs and often require extensive adjustments that stretch the time between design and implementation. Nature's creative use of biopolymer building blocks provides an alternative feedstock of manufactured scaffolds for tissue engineering applications. Plant development results in complex hierarchical structures in layers up to 1 μm in thickness, a resolution that is out of reach for most conventional manufacturing techniques. Herein, the present disclosure shows that it is possible to maintain the structural complexity of plant tissues after decellularization, and with simple biofunctionalization these surfaces can support adhesion of human cells. The highly hydrophilic nature of plant tissues and their efficacy in transport of fluids also enabled efficient expansion of human cells over extended periods of time. Human cells also sensed the topographical features of plant tissues and conformed to the structural motifs, resulting in cell patterning into concave areas, alignment along plant micropatterns, or growth around the plant vasculature. Decellularized plant tissues may provide a diverse array of complex biomaterials with limited costs. In addition, the ability to borrow scaffold structures from the plant kingdom offers the potential to shorten developmental time, while allowing mass production of complex biomaterials with low costs.

---

The invention claimed is:

1. A plant scaffold comprising a decellularized plant tissue comprising a plant adhesion molecule conjugated to a cell adhesion peptide, wherein the plant scaffold has a perfusable structure.

2. The plant scaffold as set forth in claim 1, wherein the decellularized plant tissue is selected from the group consisting of leaf tissue, stem tissue, root tissue, and combinations thereof.

3. The plant scaffold as set forth in claim 1, wherein the decellularized plant tissue is derived from a plant selected from the group consisting of spinach, sweet wormwood, parsley, vanilla, peanut, and combinations thereof.

4. The plant scaffold as set forth in claim 1, wherein the plant adhesion molecule is selected from the group consisting of a dopamine-containing compound, a polyphenol and combinations thereof.

5. The plant scaffold as set forth in claim 1, wherein the cell adhesion peptide is selected from the group consisting of RGD, RGDS (SEQ ID NO:7), CRGDS (SEQ ID NO:8), CRGDSP (SEQ ID NO:9), CPHSRNSGSGSGSGSGRGD (SEQ ID NO:29), Acetylated-GCYGRGDSPG (SEQ ID NO:30), CRDGS (SEQ ID NO:31), cyclic RGD {Fd}C (SEQ ID NO: 32), and RGDSP (SEQ ID NO:43).

6. The plant scaffold as set forth in claim 1, further comprising a mineral layer, wherein the mineral layer comprises a calcium to phosphate ratio of from about 2.5:1 to about 1:1.

7. The plant scaffold as set forth in claim 1, further comprising a mineral layer, wherein the mineral layer further comprises a biomolecule selected from the group consisting of nucleic acids, proteins, peptides, growth factors, proteoglycans, and combinations thereof.

8. The plant scaffold of claim 1, further comprising a cell.

9. The plant scaffold of claim 8, wherein the cell is a mesenchymal stem cell.

10. A method for preparing a plant scaffold for tissue engineering, the method comprising:

decellularizing a plant tissue to provide a plant scaffold having a perfusable structure; and contacting the decellularized plant tissue with a plant adhesion molecule conjugated to a cell adhesion peptide.

11. The method as set forth in claim 10, wherein the decellularizing the plant tissue comprises perfusing the plant tissue with at least one detergent.

12. The method as set forth in claim 10, wherein the plant adhesion molecule is selected from the group consisting of a dopamine-containing compound, a polyphenol and combinations thereof.

13. The method as set forth in claim 10, wherein the cell adhesion peptide is selected from the group consisting of RGD, RGDS (SEQ ID NO:7), CRGDS (SEQ ID NO:8), CRGDSP (SEQ ID NO:9), GWGGRGDSP (SEQ ID NO:11), CPHSRNSGSGSGSGSGRGD (SEQ ID NO:29), Acetylated-GCYGRGDSPG (SEQ ID NO:30), CRDGS (SEQ ID NO:31), cyclic RGD {Fd}C (SEQ ID NO:32), and RGDSP (SEQ ID NO:43).

14. The method as set forth in claim 10, wherein the plant scaffold supports vasculature above about 200 µm diffusion limit.

15. A cell culture method comprising contacting a cell with the plant scaffold as set forth in claim 1.

* * * * *

UNITED STATES PATENT AND TRADEMARK OFFICE
CERTIFICATE OF CORRECTION

| | | |
|---|---|---|
| PATENT NO. | : 12,280,177 B2 | Page 1 of 1 |
| APPLICATION NO. | : 17/388652 | |
| DATED | : April 22, 2025 | |
| INVENTOR(S) | : William L. Murphy et al. | |

It is certified that error appears in the above-identified patent and that said Letters Patent is hereby corrected as shown below:

On the Title Page

Item (72) Inventors: "Carol Cramer" should be --Carol L. Cramer--.
Item (72) Inventors: "Luis Fabircio Medina-Bolivar" should be --Luis Fabricio Medina-Bolivar--.

In the Specification

Column 11, Line 1, "phosphorin" should be --phosphoryn--.
Column 15, Line 4, "(Leica Microsystems, Buffalo Grove,Ill.)." should be --(Leica Microsystems, Buffalo Grove, IL.)--.

Signed and Sealed this
Twenty-seventh Day of May, 2025

Coke Morgan Stewart
*Acting Director of the United States Patent and Trademark Office*